US012649171B2

(12) United States Patent
Lee et al.

(10) Patent No.: US 12,649,171 B2
(45) Date of Patent: Jun. 9, 2026

(54) SPATIAL ULTRASOUND MODULATOR, ULTRASONIC APPARATUS HAVING THE SAME AND METHOD OF GENERATING AMPLITUDE-MODULATED ULTRASONIC WAVES USING THE SAME

(71) Applicant: Korea Advanced Institute of Science and Technology, Daejeon (KR)

(72) Inventors: Hyunjoo Jenny Lee, Daejeon (KR); Geon Kuk, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 264 days.

(21) Appl. No.: 18/614,474

(22) Filed: Mar. 22, 2024

(65) Prior Publication Data

US 2024/0351069 A1     Oct. 24, 2024

(30) Foreign Application Priority Data

Mar. 24, 2023     (KR) ......................... 10-2023-0038738

(51) Int. Cl.
*A61N 7/00*          (2006.01)
*B06B 1/02*          (2006.01)
(52) U.S. Cl.
CPC .......... *B06B 1/0292* (2013.01); *B06B 1/0215* (2013.01); *A61N 7/00* (2013.01); *A61N 2007/0026* (2013.01)
(58) Field of Classification Search
CPC ....... B06B 1/0215; B06B 1/0292; A61N 7/00; A61N 2007/0026
See application file for complete search history.

(56) References Cited

U.S. PATENT DOCUMENTS 10,441,975 B2 * 10/2019 Apte ...................... B06B 1/0292
11,719,671 B2 * 8/2023 Akhbari .................. G06F 3/043
                                                            73/627

(Continued)

*Primary Examiner* — Daniel L Murphy
*Assistant Examiner* — Amie M Dure
(74) *Attorney, Agent, or Firm* — Wolf, Greenfield & Sacks, P.C.

(57)          ABSTRACT

A spatial ultrasound modulator includes a signal line, an ultrasonic array, a pixel coder and an ultrasonic driver. The signal line includes a plurality of first conductive lines and a plurality of second conductive lines. The plurality of first conductive lines are arranged to be spaced apart from each other on a substrate. The plurality of second conductive lines are arranged to intersect the first conductive lines above the plurality of first conductive lines and to be spaced apart from each other. The ultrasonic array includes a plurality of ultrasonic generators. Each of the plurality of ultrasonic generators includes at least one capacitive micromachined ultrasonic transducer (CMUT) device. Each of the plurality of ultrasonic generators is superimposed on one of a plurality of pixels, which are intersection points of the plurality first conductive lines and the plurality of second conductive lines. Each of the plurality of ultrasonic generators generates a unit-ultrasonic wave. The pixel coder may be configured to generate the coding array by coding each of the plurality of pixels of the ultrasonic array so that an operation mode of each of the plurality of pixels may be a contrasting binary operation mode of the ultrasonic generator. The coding array includes active pixels and inactive pixels. The ultrasonic driver drives the coding array to generate amplitude-modulated ultrasonic waves of which a wavefront may be deformed. The amplitude-modulated ultrasonic waves are a synthesized plurality of unit-ultrasonic waves.

24 Claims, 10 Drawing Sheets

1000

(56)        References Cited

U.S. PATENT DOCUMENTS

| | | | |
|---|---|---|---|
| 2005/0177045 A1* | 8/2005 | Degertekin | G01N 29/2406 |
| | | | 600/447 |
| 2006/0230835 A1* | 10/2006 | Wang | H04R 19/00 |
| | | | 73/718 |
| 2013/0162102 A1* | 6/2013 | Sammoura | B06B 1/0603 |
| | | | 310/321 |
| 2017/0326591 A1* | 11/2017 | Apte | B06B 1/0292 |
| 2019/0164882 A1* | 5/2019 | Chen | H10D 84/834 |
| 2019/0316958 A1* | 10/2019 | Akkaraju | G01S 7/5208 |
| 2022/0169497 A1* | 6/2022 | Savoia | H04R 17/00 |
| 2022/0262791 A1* | 8/2022 | Shi | H01L 23/50 |
| 2023/0129720 A1* | 4/2023 | Giusti | G01L 9/008 |
| | | | 257/415 |
| 2024/0355819 A1* | 10/2024 | Shi | H01L 23/50 |

* cited by examiner

1000

V=0

V=V$_{pi}$ 330
320
310
210
100

V=40

400

2000

NM

PIM

NM
PIM

NM
PIM

SPATIAL ULTRASOUND MODULATOR, ULTRASONIC APPARATUS HAVING THE SAME AND METHOD OF GENERATING AMPLITUDE-MODULATED ULTRASONIC WAVES USING THE SAME

CROSS-REFERENCE TO RELATED APPLICATION

The present application claims priority from Korean Patent Application No. 10-2023-0038738, filed on Mar. 24, 2023, in the Korean Intellectual Property Office, the disclosure of which is incorporated herein in its entirety by reference.

BACKGROUND

1. Field

The present disclosure relates to a spatial ultrasound modulator, an ultrasonic apparatus having the spatial ultrasound modulator and a method of generating amplitude-modulated ultrasonic waves using the spatial ultrasound modulator. More specifically, the present disclosure pertains to a dynamic spatial ultrasound modulator capable of shaping the wavefront of ultrasonic waves in real time using a plurality of capacitive micromachined ultrasonic transducers (CMUTs), an ultrasonic apparatus having the spatial ultrasound modulator and a method of generating amplitude modulated ultrasonic waves using the spatial ultrasound modulator.

2. Description of the Related Art

Spatial ultrasonic modulators are widely used for non-destructive testing of a test target or non-invasive stimulation within a living organism that require directing ultrasonic waves into a target object without damaging the target object.

The conventional spatial ultrasound modulator includes a plurality of wave sources, each being driven by an individual driving source, and a plurality of ultrasonic waves having different phases are generated from the plurality of wave sources. Moreover, the spatial ultrasound modulator generates incident waves that are ultrasonic waves in which the generated plurality of ultrasonic waves are synthesized.

Recently, the spatial ultrasound modulators have been increasingly used in the fields where higher precision is required, such as neural stimulation technologies for stimulating fine nerves within the living organism or technologies for imaging of internal defect of ultraprecision integrated circuit devices. Therefore, technological development is required for a spatial ultrasound modulator capable of creating incident waves having a high focusing resolution.

The focusing resolution for the target region is determined by the focusing resolution of the spatial ultrasound modulator. Moreover, the focusing resolution of the spatial ultrasound modulator is determined by the number of individual wave sources that generate the ultrasonic waves.

Since the conventional spatial ultrasound modulator includes a driving unit for each wave source, the number of wave sources needs to be increased to improve the focusing resolution. In such a case, the number of driving sources for individually driving the wave sources is also increased. Accordingly, the device volume of the spatial ultrasound modulator is inevitably increased.

To address the aforementioned issues, there is a demand for a novel spatial ultrasound modulator and an ultrasonic apparatus having the same that offer high focusing resolution despite a small size.

SUMMARY

Proposed to address the aforementioned issues, an object of the present disclosure is to provide a spatial ultrasound modulator in which an ultrasonic array including a plurality of ultrasonic generators superimposed on a plurality of pixels is configured to generate amplitude-modulated ultrasonic waves, of which the wavefront may be shaped in real time.

Another object of the present disclosure is to provide an ultrasonic apparatus including the aforementioned spatial ultrasound modulator.

Yet another object of the present disclosure is to provide a method of generating amplitude-modulated ultrasonic waves, of which wavefront may be shaped in real time, using the aforementioned spatial ultrasound modulator.

A spatial ultrasound modulator in accordance with an embodiment of the present disclosure may include a signal line, an ultrasonic array, a pixel coder and an ultrasonic driver.

The signal line may include a plurality of first conductive lines and a plurality of second conductive lines. The plurality of first conductive lines may be arranged to be spaced apart from each other on a substrate. The plurality of second conductive lines may be arranged to intersect the first conductive lines above the plurality of first conductive lines and to be spaced apart from each other.

The ultrasonic array may include a plurality of ultrasonic generators. Each of the plurality of ultrasonic generators may include at least one CMUT device. Each of the plurality of ultrasonic generators may be superimposed on any one of a plurality of pixels, which are intersection points of the plurality of first conductive lines and the plurality of second conductive lines. Each of the plurality ultrasonic generators may generate unit-ultrasonic waves.

The pixel coder may generate a coding array by determining the operation mode of each of the plurality of ultrasonic generators as either a normal mode or a pull-in mode. The coding array may include an active pixel and an inactive pixel.

The ultrasonic driver may drive the coding array to generate amplitude-modulated ultrasonic waves in which the wavefront may be transformed. The amplitude-modulated ultrasonic waves may have a plurality of unit-ultrasonic waves synthesized therein.

In the spatial ultrasound modulator in accordance with an embodiment of the present disclosure, the operation mode may be one of the normal mode and the pull-in mode. When the operation mode is in the normal mode, the ultrasonic generator may operate at a first natural frequency, and the pixel superimposed on the ultrasonic generator may function as an active pixel. When the operation mode is in the pull-in mode, the ultrasonic generator may operate at a second natural frequency different from the first natural frequency, and the pixel superimposed on the ultrasonic generator may function as an inactive pixel.

The ultrasonic generator of the spatial ultrasound modulator in accordance with an embodiment of the present disclosure may include a plurality of CMUT devices. The plurality of CMUT devices may generate a plurality of fine ultrasonic waves. The unit-ultrasonic waves may have the plurality of fine ultrasonic waves synthesized therein.

The pixel coder of the spatial ultrasound modulator in accordance with an embodiment of the present disclosure may include an initialization driver, a scanline setter, a mode line setter, a pull-in coder and a timing controller.

The initialization driver may apply an initialization signal to the plurality of first conductive lines and the plurality of second conductive lines to initialize the operation mode of the plurality of ultrasonic generators to the normal mode.

The scanline setter may select any one of the plurality of second conductive lines as a scan line. The scanline setter may select a pixel row corresponding to the scan line as a coding row.

The mode line setter may select at least one of the plurality of first conductive lines as a mode changing line. The mode line setter may select a pixel column of an ultrasonic array corresponding to the mode changing line as the coding row.

The pull-in coder may apply a scan signal to the scan line. The pull-in coder may apply a mode changing signal to the mode changing line. The pull-in coder may perform a pull-in coding operation to code a coding target pixel in the pull-in mode using the potential difference between the scan signal and the mode changing signal. The coding target pixel may be a pixel located at the intersection of a coding row and a coding column.

The timing controller may control operation timing of the scanline setter and the mode line setter to successively select one of the plurality of second conductive lines as a scan line. The timing controller may select the first conductive line of the plurality of first conductive lines corresponding to the coding target pixel as the mode changing line.

The initialization signal of the spatial ultrasound modulator in accordance with an embodiment of the present disclosure may include a first partial setting signal and a second partial setting signal. The first partial setting signal corresponding to a first partial setting voltage may be applied to the plurality of first conductive lines. The second partial setting signal corresponding to a second partial setting voltage may be applied to the plurality of second conductive lines. A setting voltage may be the potential difference between the first partial setting voltage and the second partial setting voltage. The setting voltage may satisfy the condition expressed in (1) below. The setting voltage may be applied to the ultrasonic generator.

$$V_{po} < V_s = (V_{s1} - V_{s2}) < V_{pi} \qquad (1)$$

Here, Vpo may be a pull-out voltage, and Vpi may be a pull-in voltage. Vs may be a setting voltage, whereas Vs1 may be the first partial setting voltage, and Vs2 may be the second partial setting voltage.

A scan voltage of the spatial ultrasound modulator in accordance with an embodiment of the present disclosure may be a voltage of the scan signal. A mode voltage may be a voltage of the mode changing signal. When the scan voltage and the mode voltage satisfy the below conditions (2) to (4), the operation mode of the ultrasonic generator superimposed on a coding target pixel among the ultrasonic generators superimposed on a coding row may be changed to the pull-in mode. The operation mode of the ultrasonic generator not corresponding to the coding target pixel among the ultrasonic generators superimposed on the coding row may be kept in the normal mode.

4

$$Vs - V_{scan} < V_{pi} \qquad (2)$$
$$V_{mode} - V_{scan} > V_{pi} \qquad (3)$$
$$V_{mode} < V_{pi} \qquad (4)$$

In conditions (2) and (4), Vs may be the setting voltage, and Vscan may be the scan voltage, and Vmode may be the mode voltage.

When the mode voltage of the spatial ultrasound modulator in accordance with an embodiment of the present disclosure satisfies condition (5), the operation mode of the ultrasonic generator superimposed on a pull-in pixel may be kept in the pull-in mode while the pull-in coding operation is performed in a coding row corresponding to the pull-in pixel. The pull-in pixel may be a pixel that has been already coded in the pull-in mode through the pull-in coding operation.

$$Vpo < Vmode < Vpi \qquad (5)$$

The pixel coder of the spatial ultrasound modulator in accordance with an embodiment of the present disclosure may further include a pixel reset unit configured to reset a coded pixel.

The ultrasonic driver of the spatial ultrasound modulator in accordance with an embodiment of the present disclosure may include a drive setting unit and a driving unit.

The drive setting unit may control the bias voltages applied to the plurality of ultrasonic generators of the coding array to be the same with each other by applying a drive-bias to the coding array.

The driving unit may control the ultrasonic generator corresponding to the active pixel to generate unit ultrasonic waves by applying a drive signal to the coding array.

The drive setting unit of the spatial ultrasound modulator in accordance with an embodiment of the present disclosure may apply a drive-bias satisfying the below condition (6) to the plurality of first conductive lines. The drive setting unit may control the plurality of second conductive lines to be grounded.

$$Vpo < Vd < Vpi \qquad (6)$$

Here, Vpo may be a pull-out voltage, and Vpi may be a pull-in voltage, whereas Vd may be a drive-bias.

The frequency of the drive signal of the spatial ultrasound modulator in accordance with an embodiment of the present disclosure may be the same as the natural frequency of the ultrasonic generator operating in the normal mode.

The spatial ultrasound modulator in accordance with an embodiment of the present disclosure may further include a waveform controller. The waveform controller may be configured to control the pixel coder to change the coding array according to wavefront information. The waveform controller may control the ultrasonic driver to generate amplitude-modulated ultrasonic waves according to the changed coding array to deform the wavefront of the amplitude-modulated ultrasonic waves in real time.

An ultrasonic apparatus in accordance with an embodiment of the present disclosure may include a wavefront information setter, a spatial ultrasound modulator and a response detection unit.

The wavefront information setter may be configured to set wavefront information corresponding to incident waves. The incident waves may be spatially modulated ultrasonic waves incident on a target object.

The spatial ultrasound modulator may include a pixel coder and an ultrasonic driver.

The pixel coder may be configured to code the ultrasonic array based on the wavefront information to generate the coding array. The coding array may include an active pixel and an inactive pixel. The ultrasonic array may include a plurality of ultrasonic generators. Each of the plurality of ultrasonic generators may include at least one capacitive micromachined ultrasonic transducer (CMUT) device. Each of the plurality of ultrasonic generators may be superimposed on any one of a plurality of pixels. The ultrasonic driver may be configured to drive the coding array to generate amplitude-modulated ultrasonic waves having a wavefront corresponding to the wavefront information.

The response detection unit may be configured to detect a response of the target object to the incident waves.

The spatial ultrasound modulator of the ultrasonic apparatus in accordance with an embodiment of the present disclosure may further include a signal line including a plurality of first conductive lines and a plurality of second conductive lines.

The plurality of first conductive lines may be arranged to be spaced apart from each other on a substrate. The plurality of second conductive lines may be arranged to intersect the plurality of first conductive lines above the plurality of first conductive lines and to be spaced apart from each other. The bias voltage applied to the ultrasonic generator may be a potential difference between any one of the plurality of first conductive lines and any one of the plurality of second conductive lines.

The pixel coder of the ultrasonic apparatus in accordance with an embodiment of the present disclosure may include an initialization driver, a scanline setter, a mode line setter, a pull-in coder and a timing controller.

The initialization driver may apply an initialization signal to the plurality of first conductive lines and the plurality of second conductive lines to initialize the operation mode of each of the plurality of ultrasonic generators to a normal mode.

The scanline setter may select any one of the plurality of second conductive lines as a scan line for transmitting a scan signal. The scanline setter may select a pixel row, which is the ultrasonic generators among the plurality of ultrasonic generators corresponding to the scan line, as a coding row.

The mode line setter may select at least one of the plurality of first conductive lines as a mode changing line for transmitting a mode changing signal. The mode changing signal may be for changing the operation mode of the ultrasonic generator to any one of the normal mode and the pull-in mode. The mode line setter may select a pixel column, which is the ultrasonic generators among the plurality of ultrasonic generators corresponding to the mode changing line, as the coding column.

The pull-in coder may apply the scan signal to the scan line. The pull-in coder may apply the mode changing signal to the mode changing line. The pull-in coder may perform a pull-in coding operation, which is configured to code a coding target pixel in the pull-in mode using the potential difference between the scan signal and the mode changing signal. The coding target pixel may be a pixel located at an intersection of a coding row and a coding column.

The timing controller may be configured to control the scanline setter to successively select each of the plurality of second conductive lines as the scan line. The timing controller may be configured to control the mode line setter to select the first conductive line of the plurality of the first conductive lines corresponding to the coding target pixel as the mode changing line. The timing controller may be configured to control the pull-in coder to perform the pull-in coding operation.

The initialization signal of the ultrasonic apparatus in accordance with an embodiment of the present disclosure may include a first partial setting signal and a second partial setting signal. The first partial setting signal corresponding to a first partial setting voltage may be simultaneously applied to the plurality of first conductive lines. The second partial setting signal corresponding to a second partial setting voltage may be simultaneously applied to the plurality of second conductive lines. A setting voltage may be the potential difference between the first partial setting voltage and the second partial setting voltage. The setting voltage may satisfy the condition expressed in (1) below. The setting voltage may be applied to the ultrasonic generator.

$$V_{po} < V_s = (V_{s1} - V_{s2}) < V_{pi} \qquad (1)$$

Here, Vpo may be a pull-out voltage, and Vpi may be a pull-in voltage. Vs may be a setting voltage, whereas Vs1 may be the first partial setting voltage, and Vs2 may be the second partial setting voltage.

A scan voltage may be a voltage of the scan signal. A mode voltage may be a voltage of the mode changing signal. When the scan voltage and the mode voltage satisfy the below conditions (2) to (4), a bias voltage greater than the pull-in voltage may be applied to the ultrasonic generator corresponding to the coding target pixel, resulting in changing the operation mode of the ultrasonic generator to the pull-in mode and maintaining the operation mode of the ultrasonic generator not corresponding to the coding target pixel in the normal $$V_s - V_{scan} < V_{pi} \qquad (2)$$
$$V_{mode} - V_{scan} > V_{pi} \qquad (3)$$
$$V_{mode} < V_{pi} \qquad (4)$$

In conditions (2) and (4), Vs may be the setting voltage, and Vscan may be the scan voltage, and Vmode may be the mode voltage.

When the mode voltage satisfies condition (5), the operation mode of the ultrasonic generator superimposed on a pull-in pixel may be maintained in the pull-in mode while the pull-in coding operation is performed in a coding row corresponding to the pull-in pixel. The pull-in pixel may be a pixel that has been already coded in the pull-in mode through the pull-in coding operation.

$$V_{po} < V_{mode} < V_{pi} \qquad (5)$$

The ultrasonic driver of the ultrasonic apparatus in accordance with an embodiment of the present disclosure may include a drive setting unit and a driving unit.

The drive setting unit may apply a drive-bias satisfying the below condition (6) to the plurality of first conductive lines. The drive setting unit may control the plurality of second conductive lines to be grounded.

$$V_{po} < V_d < V_{pi} \qquad (6)$$

Here, Vpo may be a pull-out voltage, and Vpi may be a pull-in voltage, whereas Vd may be a drive-bias.

The driving unit may control the ultrasonic generator corresponding to the active pixel to generate unit ultrasonic waves by applying a drive signal to the coding array.

The drive signal of the ultrasonic apparatus in accordance with an embodiment of the present disclosure may include an AC signal. The frequency of the AC signal may be the same as the natural frequency of the ultrasonic generator that is operating in the normal mode. The method of generating amplitude-modulated ultrasonic waves in accordance with an embodiment of the present disclosure may include step 1, step 2, step 3 and step 4.

In step 1, an ultrasonic array may include a plurality of pixel rows and a plurality of pixel columns. The pixel rows and the pixel columns may each include a plurality of ultrasonic generators. Each of the plurality of ultrasonic generators may be superimposed on any one of a plurality of pixels. An ultrasonic array may be initialized by a setting voltage such that the plurality of ultrasonic generators operate in a normal mode.

In step 2, the plurality of pixel rows may be successively selected, one by one, as a coding row. At least one pixel column of the plurality of pixel columns that corresponds to a coding target pixel may be selected as a coding column.

In step 3, a coding array may include an active pixel and an inactive pixel. When the operation mode is in the normal mode, the ultrasonic generator may operate at a first natural frequency, and the pixel superimposed on the ultrasonic generator may function as an active pixel. When the operation mode is in the pull-in mode, the ultrasonic generator may operate at a second natural frequency different from the first natural frequency, and the pixel superimposed on the ultrasonic generator may function as an inactive pixel. Every time a coding row is selected, a scan voltage and a mode voltage are applied to the coding row and the coding column, respectively, and the operation mode of the ultrasonic generator superimposed on the coding target pixel may be changed to the pull-in mode. Alternatively, the coding array may be created.

In step 4, the coding array may generate amplitude-modulated ultrasonic waves in which the wavefront may be modified. The amplitude-modulated ultrasonic waves may be a synthesized plurality of unit-ultrasonic waves, each of which is generated by an ultrasonic generator superimposed on an active pixel.

In step 1 of the method of generating amplitude-modulated ultrasonic waves in accordance with an embodiment of the present disclosure, the plurality of pixel rows may be grounded. A setting voltage satisfying the condition expressed in (1) below may be applied to a plurality of pixel columns.

$$V_{po} < V_s = (V_{s1} - V_{s2}) < V_{pi} \qquad (1)$$

Here, Vpo may be a pull-out voltage, and Vpi may be a pull-in voltage. Vs may be a setting voltage, whereas Vs1 may be a first partial setting voltage, and Vs2 may be a second partial setting voltage.

In step 3 of the method of generating amplitude-modulated ultrasonic waves in accordance with an embodiment of the present disclosure, when the setting voltage, the scan voltage and the mode voltage satisfy conditions (2) to (4) shown below, the operation mode of the ultrasonic generator of the plurality of ultrasonic generators superimposed on the coding row that is not superimposed on the coding target pixel may be maintained in the normal mode.

$$V_s - V_{scan} < V_{pi} \qquad (2)$$

$$V_{mode} - V_{scan} > V_{pi} \qquad (3)$$

$$V_{mode} < V_{pi} \qquad (4)$$

In conditions (2) and (4), Vs may be the setting voltage, and Vscan may be the scan voltage, and Vmode may be the mode voltage.

When the mode voltage of the method of generating amplitude-modulated ultrasonic waves in accordance with an embodiment of the present disclosure satisfies condition (5), the operation mode of the ultrasonic generator superimposed on a pull-in pixel may be kept in the pull-in mode while the pull-in coding operation is performed for a coding row corresponding to the coding target pixel. The pull-in pixel may be a pixel that has been already coded in the pull-in mode through the pull-in coding operation.

$$V_{po} < V_{mode} < V_{pi}. \qquad (5)$$

The method of generating amplitude-modulated ultrasonic waves in accordance with an embodiment of the present disclosure may further include step 3-1, in which the coding row may be grounded. Moreover, a drive-bias satisfying condition (6) expressed below may be applied to a coding column such that the operation mode of the ultrasonic generator superimposed on the pull-in pixel may be maintained in the pull-in mode. Step 3-1 may be carried out after step 3 and before step 4. The pull-in pixel may be a pixel that has been coded in the pull-in mode through the pull-in coding operation.

$$V_{po} < V_d < V_{pi} \qquad (6)$$

Here, Vpo may be a pull-out voltage, and Vpi may be a pull-in voltage, whereas Vd may be a drive-bias.

In step 4 of the method of generating amplitude-modulated ultrasonic waves in accordance with an embodiment of the present disclosure, a drive signal may be applied to the coding array. Moreover, the drive signal may be an AC signal having the same frequency as the first natural frequency.

According to an embodiment of the present disclosure, it is possible to provide a spatial ultrasound modulator in which an ultrasonic array including a plurality of ultrasonic generators superimposed on a plurality of pixels generate amplitude-modulated ultrasonic waves, of which wavefront may be shaped in real time, an ultrasonic apparatus including the spatial ultrasound modulator and a method of generating amplitude-modulated ultrasonic waves using the spatial ultrasound modulator.

The plurality of ultrasonic generators may be coded with one of the normal mode and the pull-in mode to generate a coding array. Each of the plurality of ultrasonic generators may include at least one CMUT device. The ultrasonic array may include a plurality of ultrasonic generators, each of which is superimposed on any one of a plurality of pixels. The coding array may include an active pixel and an inactive pixel.

When a drive signal having the same frequency as the natural frequency of the ultrasonic generator operating in the normal mode is applied to the coding array, unit-ultrasonic waves may be generated in the active pixels only, and the unit-ultrasonic waves may not be generated in the inactive pixels. That is, a plurality of amplitude-modulated ultrasonic waves having different shapes of wavefront may be generated based on a pixel map.

The operation mode of the plurality of ultrasonic generators of the coding array may be changed based on the scan voltage, the mode voltage and the setting voltage. Therefore, users may readily change the coding array by changing the scan voltage, the mode voltage and/or the setting voltage. In other words, with the present disclosure, the shape of the wavefront of the amplitude-modulated ultrasonic waves may be changed by changing the scan voltage, the mode voltage and/or the setting voltage. Moreover, increasing the degree of integration of the ultrasonic generators may improve the focusing resolution.

DETAILED DESCRIPTIONS

Hereinafter, certain preferred embodiments of the present disclosure will be described with reference to the accompanied drawings, but the described embodiments are not intended to limit the present disclosure thereto, and anyone of ordinary skill in the art to which the present disclosure pertains shall be able to embody the present disclosure in various other forms without departing from the technical ideas of the present disclosure.

In the accompanied drawings, the dimensions of substrates, layers (or membranes), areas, patterns or structures are exaggerated for the sake of clarity of the present disclosure. In the present disclosure, when a substrate, layer (or membrane), area, pattern or structure is described to be formed "on," "above" or "below" the other substrate, layer (or membrane), area, pattern or structure, such a substrate, layer (or membrane), area, pattern or structure may be formed directly on, above or below the other substrate, layer (or membrane), area, pattern or structure, or another substrate, layer (or membrane), area, pattern or structure may be additionally formed on the other substrate, layer (or membrane), area, pattern or structure. Moreover, terms such as "first," "second" and "third" used to describe materials, layers (or membranes), areas, electrodes, patterns or structures are not intended to limit these members to these terms but to distinguish the materials, layers (or membranes), areas, electrodes, patterns or structures from each other. Accordingly, the terms such as "first," "second" and "third" may be used selectively or interchangeably for each of the materials, layers (or membranes), areas, electrodes, patterns or structures.

Figure 1:
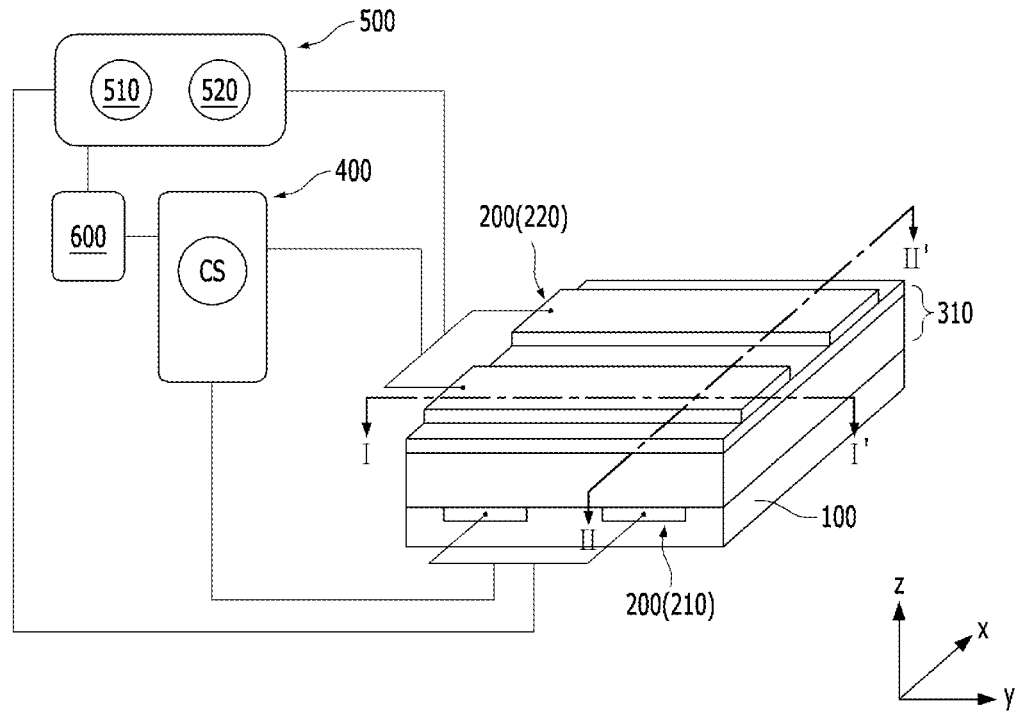
FIG. 1 illustrates an exemplary spatial ultrasound modulator in accordance with an embodiment of the present disclosure.
Figure 2A:
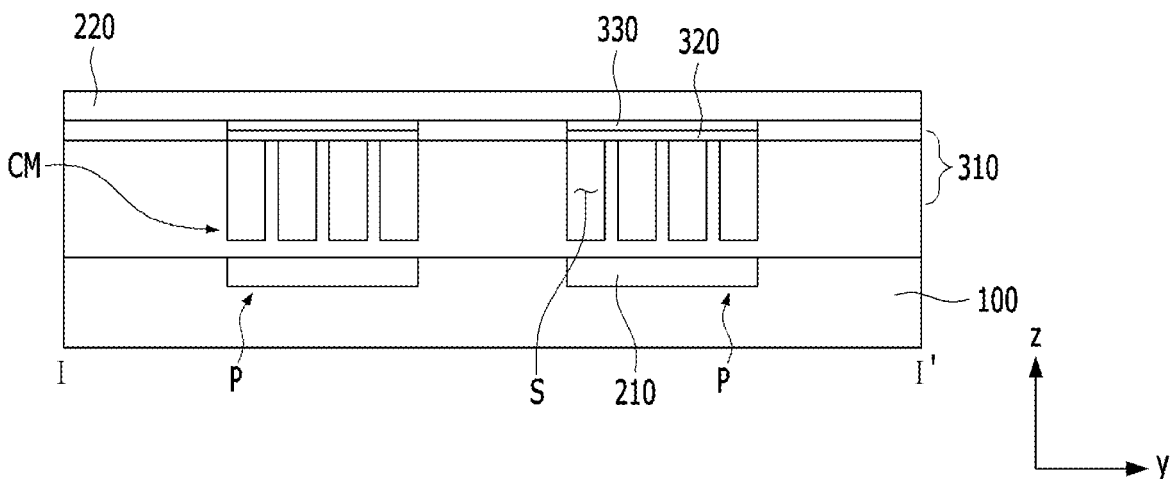
FIG. 2A illustrates a sectional view of the spatial ultrasound modulator shown in FIG. 1 along the I-I' line.
Figure 2B:
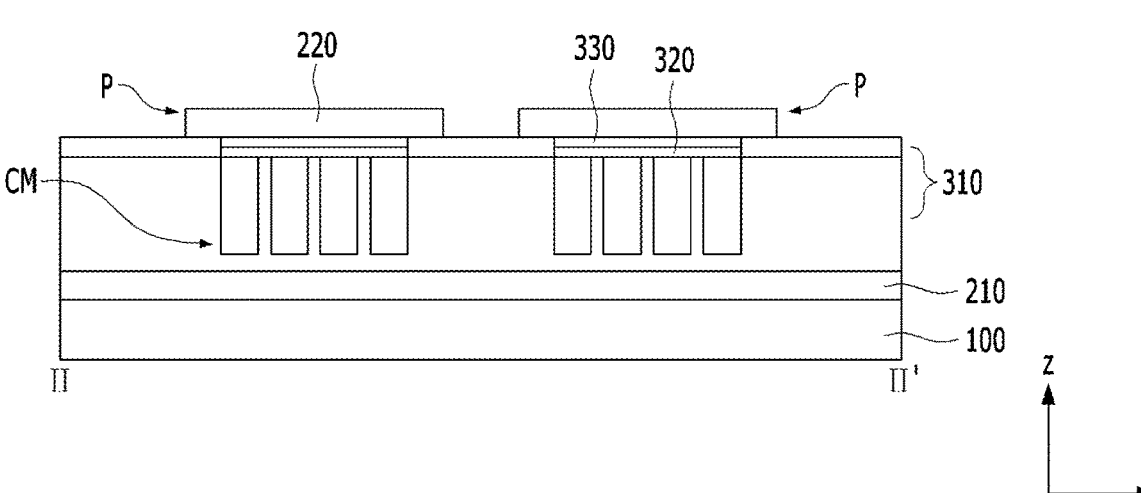
FIG. 2B illustrates a sectional view of the spatial ultrasound modulator shown in FIG. 1 along the II-II' line.
Figure 3:
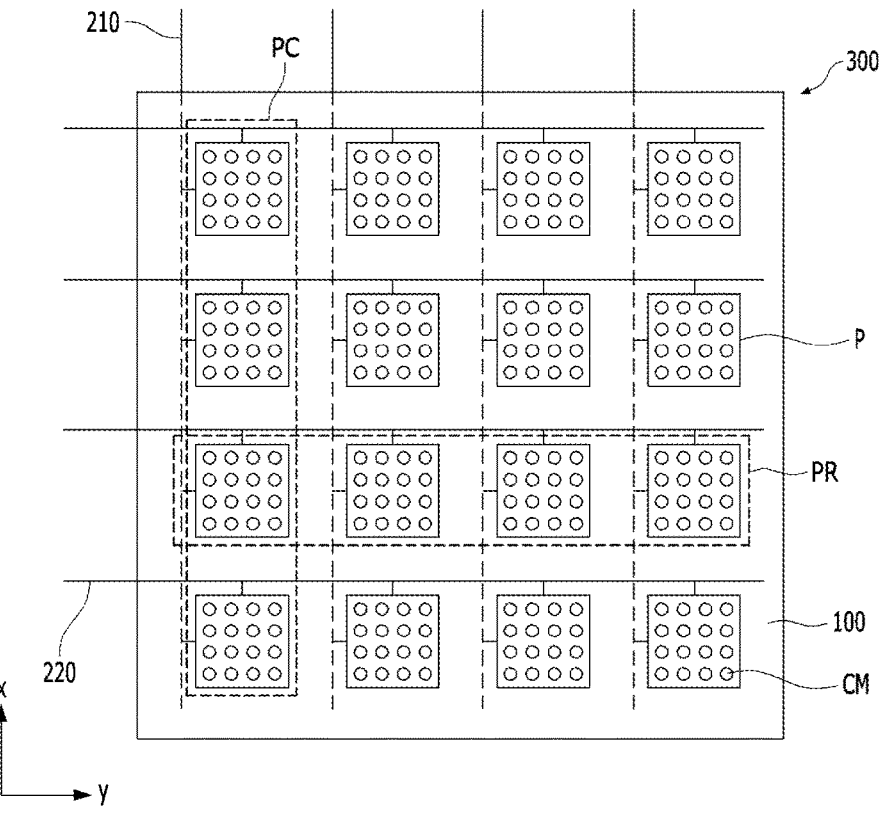
FIG. 3 illustrates a top view of an ultrasonic array of the spatial ultrasound modulator shown in FIG. 1.

FIG. 1 is an exemplary illustration of a spatial ultrasound modulator 1000 in accordance with an embodiment of the present disclosure. FIG. 2A illustrates a sectional view of the spatial ultrasound modulator 1000 shown in FIG. 1 along the I-I' line, and FIG. 2B illustrates a sectional view of the spatial ultrasound modulator 1000 shown in FIG. 1 along the II-II' line. FIG. 3 illustrates a top view of an ultrasonic array of the spatial ultrasound modulator 1000 shown in FIG. 1.

Referring to FIG. 1 to FIG. 3, the spatial ultrasound modulator 1000 in accordance with an embodiment of the present disclosure may include a substrate 100, a signal line 200, an ultrasonic array 300, a pixel coder 400, an ultrasonic driver 500 and a waveform controller 600.

The signal line 200 may include first conductive lines 210 and second conductive lines 220. The first conductive lines 210 and the second conductive lines 220 may be arranged to intersect each other along a third direction (z) on the substrate 100. The third direction (z) may be perpendicular to an upper surface of the substrate 100.

Figure 4:
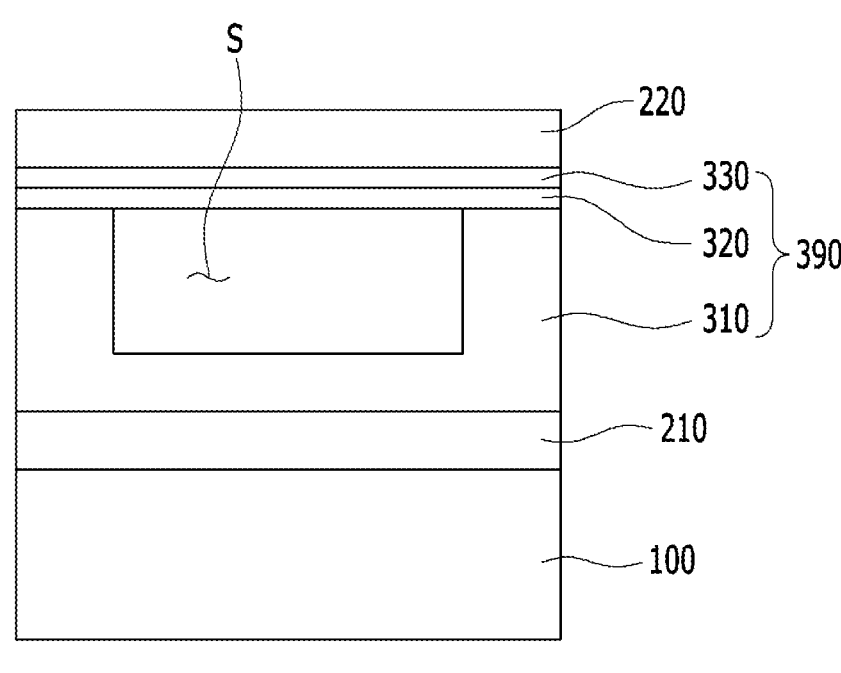
FIG. 4 is a sectional view of a portion of an ultrasonic generator.

The ultrasonic array 300 may include a plurality of ultrasonic generators 390 (see FIG. 4). Each of the plurality of ultrasonic generators 390 may be superimposed on any one of a plurality of pixels P, which are intersections of the plurality first conductive lines 210 and the plurality of second conductive lines 220.

Figure 7:
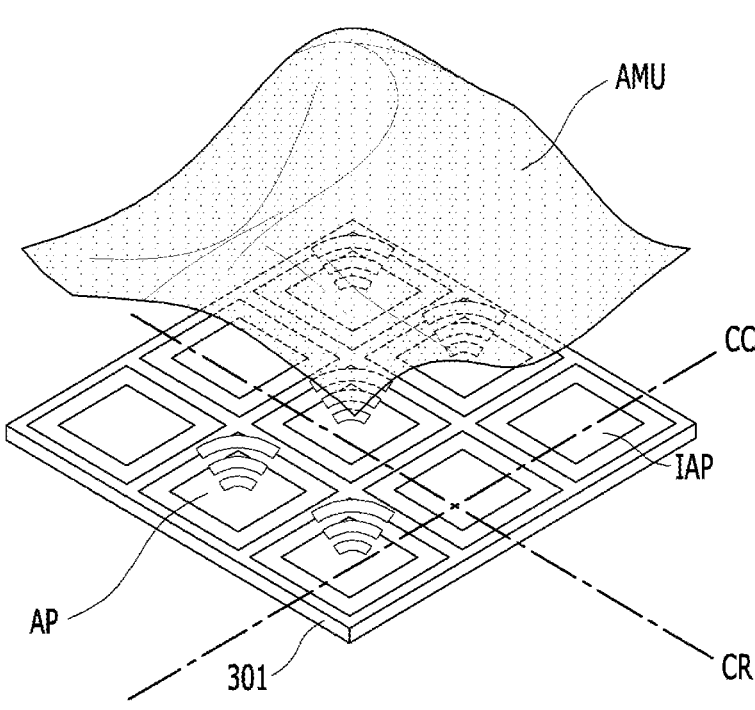
FIG. 7 illustrates an exemplary generation of amplitude-modulated ultrasonic waves from a coding array.

The pixel coder 400 may be configured to code the ultrasonic array 300 to generate a coding array 301 (see FIG. 7). That is, the pixel coder 400 may code the plurality of ultrasonic generators 390 that are superimposed on the plurality of pixels P. In this description, "coding" refers to a process in which the operation mode of an ultrasonic generator 390 superimposed on a certain pixel P is changed. For example, when it is described that a pixel is coded or an ultrasonic generator is coded, it may be interpreted that the operation mode of the ultrasonic generator superimposed on the pixel is changed.

The coding array 301 (see FIG. 7) may include an active pixel AP (see FIG. 7) and an inactive pixel IAP (see FIG. 7).

The ultrasonic driver 500 may be configured to drive the coding array 301 to generate amplitude-modulated ultrasonic waves AMU (see FIG. 7).

The waveform controller 600 may be configured to change the shape of the waveform of the amplitude-modulated ultrasonic waves AMU in real time.

In an embodiment of the present disclosure, the spatial ultrasound modulator 1000 may be configured to perform functions similar to those of a spatial light modulator (SLM), which is configured to shape the wavefront of light holo-gram. That is, the spatial ultrasound modulator 1000 may be configured to shape the wavefront of the focused ultrasonic waves to meet the purpose.

In an embodiment of the present disclosure, the substrate 100 may be a structure constituting a base of the spatial ultrasound modulator 1000. Moreover, placed on the substrate 100 may be the first conductive lines 210, the second conductive lines 220 and the ultrasonic array 300. The plurality of ultrasonic generators 390 of the ultrasonic array 300 may be interposed between the plurality of first conductive lines 210 and the plurality of second conductive lines 220.

For instance, the substrate 100 may be used as a base substrate for performing a micro-electro mechanical system (MEMS) process for forming unit cells that constitute the spatial ultrasound modulator 1000. Moreover, the substrate 100 is made of a semiconductor material, such as silicon or gallium.

The plurality of ultrasonic generators 390 may be disposed on the substrate 100. Therefore, the substrate 100 may be a useful semiconductor substrate for manufacturing the plurality of first conductive lines 210 and the plurality of CMUT devices CM. The plurality of first conductive lines 210 may be for applying a drive signal. The CMUT devices CM may be a capacitive micromachined ultrasonic transducer (CMUT).

Each of the plurality of ultrasonic generators 390 may include at least one CMUT device CM. Since the CMUT device CM functions as a capacitor, the CMUT device CM may detect ultrasonic waves pursuant to charging and discharging electrical energy.

Referring to FIG. 2A, in an embodiment of the present disclosure, the plurality of first conductive lines 210 may be interposed between one surface of the substrate 100 and an insulation film 310. Moreover, the substrate 100 may have a relatively high resistance. For example, the substrate 100 may be a part of a silicon wafer.

The substrate 100 may be rectangular. The substrate 100 may have a length in a first direction (x) and a width in a second direction (y). The second direction (y) may be substantially perpendicular to the first direction (x). However, this is merely an example, and the shape of the substrate 100 may be properly modified based on the shape of the ultrasonic driver 500. The plurality of first conductive lines 210 and the plurality of second conductive lines 220 may be spaced apart in a third direction (z) on one side of the substrate 100. The third direction (z) may be perpendicular to the first direction (x) and the second direction (y).

The plurality of first conductive lines 210 may be disposed on the substrate 100. For instance, each of the plurality of first conductive lines 210 may extend along the first direction (x). Moreover, the first conductive lines 210 may be spaced apart along the second direction (y). Since an insulating layer (not shown) is interposed between adjacent first conductive lines, the adjacent first conductive lines may be insulated from each other. Accordingly, it is possible to prevent an interference between a plurality of mode changing signals applied to the plurality of first conductive lines 210.

A pull-in coder 440 (see FIG. 6) may be configured to generate a mode changing signal for changing the operation mode of the ultrasonic generator 390. The pull-in coder 440 may be configured to change the operation mode of the ultrasonic generator 390 corresponding to a pixel P to which signals are simultaneously applied from any one of the plurality of first conductive lines 210 and any one of the plurality of second conductive lines 220.

Therefore, each of the plurality of first conductive lines 210 may include a material having a low resistance to minimize a delay in signal transmission and signal conversion. For example, the first conductive line 210 may include any one of copper, aluminum and tungsten.

After the insulating layer (not shown) covering the substrate 100 is formed, the insulating layer may be partially removed to form a plurality of trenches. Moreover, each of the plurality of trenches may extend in the first direction (x). Moreover, the plurality of trenches may be spaced apart at regular intervals along the second direction (y). Moreover, the plurality of trenches may be filled with a conductive material to form the plurality of first conductive lines 210.

Referring to FIG. 1, the plurality of ultrasonic generators 390 may be spaced apart from each other at regular intervals along the second direction (y).

Moreover, certain ultrasonic generators of the plurality of ultrasonic generators 390 may be disposed to be adjacent to one of the plurality of first conductive lines 210 and electrically connected to one of the plurality of second conductive lines 220.

Moreover, other ultrasonic generators of the plurality of ultrasonic generators 390 may be disposed to be adjacent to another one of the plurality of first conductive lines 210 and electrically connected to another one of the plurality of second conductive lines 220.

Each of the plurality of second conductive lines 220 may be spaced apart from the plurality of first conductive lines 210 and extend along the second direction (y). Moreover, the plurality of second conductive lines 220 may be spaced apart from each other along the first direction (x). Moreover, the plurality of second conductive lines 220 may be arranged to intersect the plurality of first conductive lines 210.

Referring to FIGS. 3 and 4, each of the plurality of ultrasonic generators 390 may be arranged to be superimposed on a pixel P that is an intersecting point between one of the plurality of first conductive lines 210 and one of the plurality of second conductive lines 220. That is, the plurality of ultrasonic generators 390 may be electrically connected with one of the plurality of first conductive lines 210 and one of the plurality of second conductive lines 220. Accordingly, the plurality of ultrasonic generators 390 of the ultrasonic array 300 may be superimposed on a plurality of pixels P arranged in a matrix shape along the first direction (x) and the second direction (y) on the substrate 100.

Referring to FIG. 3, the ultrasonic array 300 may be superimposed on a plurality of pixels P. The ultrasonic array 300 may include a plurality of ultrasonic generators, each of which is superimposed on one of the plurality of pixels. The plurality of pixels P may be arranged in a matrix shape. The ultrasonic array 300 may include a plurality of pixel columns PC and a plurality of pixel rows PR. The ultrasonic generators being superimposed on one of the plurality of pixels may be arranged in a rectangular shape.

A pixel column PC is defined as a plurality of ultrasonic generators arranged along the first direction (x). The plurality of pixel rows PR may be arranged to be spaced apart along the second direction (y).

A pixel row PR is defined as a plurality of ultrasonic generators arranged along the second direction (y). Moreover, the plurality of pixel rows PR may be arranged to be spaced apart along the first direction (x).

A scan signal for selecting a coding row from the plurality of pixel rows PR may be transmitted through at least one of the plurality of second conductive lines 220. Therefore, each of the plurality of second conductive lines 220 may include a material having a low resistance to minimize a delay in signal transmission and signal conversion.

A bias voltage pursuant to the scan signal and the mode changing signal may be applied to the plurality of ultrasonic generators through the plurality of first conductive lines 210 and the plurality of second conductive lines 220.

The plurality of CMUT devices CM of the ultrasonic generator 390 may be configured to generate a plurality of fine ultrasonic waves according to the scan signal and the mode changing signal. Unit-ultrasonic waves generated by the ultrasonic generator 390 may be a synthesis of the plurality of fine ultrasonic waves generated by the plurality of CMUT devices CM. The plurality of unit-ultrasonic waves may be synthesized to generate a single amplitude-modulated ultrasonic wave.

FIG. 4 is a sectional view of a portion of an ultrasonic generator 390.

Referring to FIG. 4, the CMUT device CM may include an insulation film 310, a membrane 320 and an electrode pad 330.

The insulation film 310 may cover the substrate 100.

The membrane 320 may cover the insulation film 310.

A recess covered by the insulation film 310 and membrane 320 may be defined. The recess may be interposed between the insulation film 310 and the membrane 320 and may have a predetermined depth. The recess may be a sealed space S defined by the insulation film 310 and the membrane 320. The recess may be an area caved in by a predetermined depth from one surface of the insulation film 310. Therefore, the sealed space S may be a three-dimensional space sealed by the insulation film 310 and the membrane 320.

In an embodiment of the present disclosure, the sealed space S may be maintained in vacuum. The sealed space S may reduce a deformation and air resistance caused by vibrations of the membrane 320. That is, keeping the sealed space S in the vacuum state may improve the conversion efficiency between electrical energy and acoustic energy.

The electrode pad 330 may be disposed on the membrane 320. The electrode pad 330 may be electrically connected to one of the plurality of second conductive lines 220.

The insulation film 310 may be interposed between one of the plurality of first conductive lines 210 and one of the plurality of second conductive lines 220. The one of the plurality of first conductive lines 210 and the one of the plurality of second conductive lines 220 may be spaced apart along the third direction (z).

The insulation film 310 may have a predetermined thickness. The insulation film 310 may include a material having a predetermined permittivity. The insulation film 310 may function as a capacitor between the electrode pad 330 and one of the plurality of first conductive lines 210. The electrode pad 330 may be connected with the second conductive lines 220.

In an embodiment of the present disclosure, the substrate 100 may include silicon. Each of the plurality of first conductive lines 210 may include a conductive material. The insulation film 310 may include a material that is highly adhesive to one of silicon and the first conductive lines 210.

In an embodiment of the present disclosure, the plurality of first conductive lines 210 may be disposed on the substrate 100. Although not illustrated, the insulation film 310 may be arranged to be alternatingly in contact with the substrate 100 and the first conductive lines 210. That is, the plurality of first conductive lines 210 may be arranged on one surfaced of the substrate 100, and the insulation film 310 may be arranged to cover the other surface of the substrate 100. It shall be appreciated however that this is merely an example and the present disclosure is not limited to this example.

The membrane 320 may include a semiconductor material. Moreover, the membrane 320 may be a film that vibrates according to charging and discharging of electrostatic charge stored in a capacitor. Since the sealed space S is formed by having the insulation film 310 covered by the membrane 320, it is preferable that the membrane 320 includes a material that is readily coupled with the insulation film 310 to seal the sealed space S from the outside.

When the bias voltage applied to the ultrasonic generators is a pull-in voltage, the membrane 320 may be deformed by the vibrations in the third direction (z) and make contact with the insulation film 310, which is the bottom surface of the sealed space S.

The depth of the sealed space S may be designed such that a proper pull-in voltage Vpi is determined by considering the detection sensitivity of ultrasonic waves and the physical properties of the membrane 320. The depth of the sealed space S may be the length of the sealed space S measured in the third direction (z).

Referring to FIGS. 2A, 2B and 4, each of the plurality of recesses may be a CMUT device CM. The plurality of recesses may be defined by a single membrane 320. Each of the plurality of ultrasonic generators 390 superimposed on a plurality of pixels may include at least one recess defined by a single membrane 320.

Referring to FIG. 4, the electrode pad 330 may function as a common electrode for apply a bias voltage to the plurality of CMUT devices CM. The electrode pad 330 may be disposed on one surface of the membrane 320. The electrode pad 330 may include an elastic material. The electrode pad 330 may be in contact with at least one of the plurality of second conductive lines 220. Therefore, the scan signal applied to the second conductive lines 220 may be transferred to the plurality of CMUT devices CM via the electrode pad 330. That is, it is possible to have the same scan signal transferred to the plurality of CMUT devices CM.

In an embodiment of the present disclosure, the membrane 320 and the electrode pad 330 may be a single element that is not distinguishable from each other, unlike the above description.

When a pull-in voltage Vpi (see FIG. 5a) is applied to the CMUT device CM, the membrane 320 may be deformed and make contact with the insulation film 310, which is the bottom surface of the sealed space S. That is, the pull-in voltage Vpi may be a collapse state voltage of the CMUT device CM. In the present specification, such a CMUT device CM is defined as a deformed CMUT device.

The electrode pad 330 is configured to be capable of absorbing the deformation of the membrane 320 occurred when the operation mode of the ultrasonic generator 390, i.e., the CMUT device CM, is changed to a pull-in mode or a normal mode. Moreover, the electrode pad 330 may be elastic enough to restrain the deformation of the membrane 320 described above from being transferred to the plurality of second conductive lines 220.

The first conductive lines 210 may be configured to function as an electrode for applying a bias voltage to the plurality of CMUT devices CM. Moreover, the mode changing signal may be applied to the plurality of CMUT devices CM via the plurality of first conductive lines 210. That is, it is possible to have the same mode changing signal applied to the plurality of CMUT devices CM.

Accordingly, the plurality of CMUT devices CM of the ultrasonic generator 390 may be driven in an identical fashion depending on the scan signal and the mode changing signal. That is, the plurality of CMUT devices CM of the ultrasonic generators 390 may be understood as a single virtual CMUT device of which the operation mode is determined depending on the scan signal or the mode changing signal. Moreover, changing the scan signal and the mode changing signal may result in a change of the operation mode of each of the plurality of ultrasonic generators.

The operation mode of the ultrasonic generator 390 may be one of the normal mode and the pull-in mode.

Figure 5A:
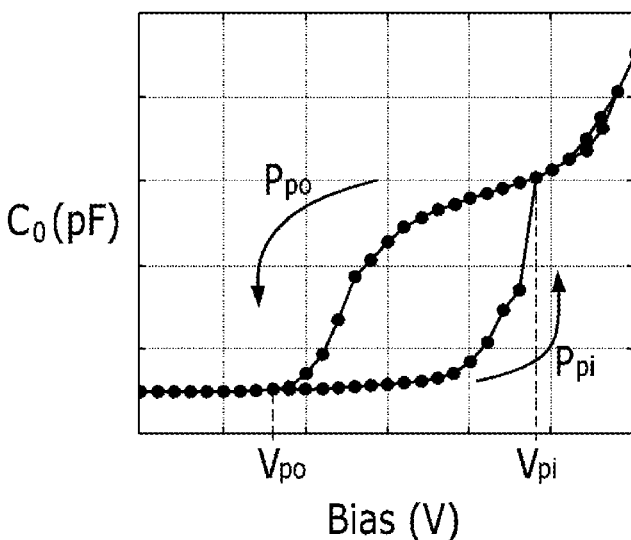
FIG. 5A is a graphical illustration of the relations between the bias voltage applied to a CMUT device and the capacitance of the CMUT device.

FIG. 5A is a graphical illustration of the relations between the bias voltage Bias (V) applied to a CMUT device CM and the capacitance C0(pF) of the CMUT device CM.

Referring to FIG. 5A, the capacitance C0(pF) of the CMUT device CM may change differently depending on the direction of change of the bias voltage Bias (V) applied to the CMUT device CM.

Hereinafter, the change of the operation mode of the ultrasonic generator 390 will be described with reference to FIG. 5A.

When the ultrasonic generator 390 is operating in the normal mode, the operation mode of the ultrasonic generator 3900 may be changed to the pull-in mode if the bias voltage Bias (V) is increased to be greater than or equal to the pull-in voltage Vpi. Here, the capacitance C0(pF) of the CMUT device CM of the ultrasonic generator 390 may vary depending on a pull-in path Ppi. The first natural frequency may be the natural frequency of the ultrasonic generator 390 of which the operation mode is the normal mode. The ultrasonic generator 390 may be driven by a drive signal having the same frequency as the first natural frequency. Moreover, the pixel corresponding to the ultrasonic generator 390 of which the operation mode is the normal mode may function as an active pixel AP (see FIG. 7).

As described later in greater detail in connection with the ultrasonic driver 500, the drive-bias may be for determining the operation mode of the ultrasonic generator, and the drive signal may be for controlling the ultrasonic generator to generate unit-ultrasonic waves.

Specifically, once the bias voltage Bias (V) reaches the pull-in voltage Vpi, the membrane 320 may make contact with the insulation film 310, which is the bottom surface of the sealed space S, to deform the sealed space S. The pull-in voltage Vpi may be a unique value of the CMUT device CM. When the membrane 320 makes contact with the insulation film 310, the natural frequency of the CMUT device CM may vary. That is, when the membrane 320 makes contact with the insulation film 310, the CMUT device CM may operate as a deformed CMUT device. The first natural frequency, which is the natural frequency of the undeformed CMUT device CM, may be different from the second natural frequency, which is the natural frequency of the deformed CMUT device. That is, the natural frequency of the ultrasonic generator 390 of which the operation mode is the pull-in mode may be the second natural frequency. The ultrasonic generator 390 of which the operation mode is the pull-in mode may have a different natural frequency from that of the ultrasonic generator 390 of which the operation mode is the normal mode.

Therefore, in the case where a drive signal having the same frequency as the first natural frequency is applied to the deformed CMUT device, it is not possible to generate ultrasonic wave by vibrating the membrane 320. The ultrasonic generator 390 of which the operation mode is the pull-in mode may hardly generate unit-ultrasonic waves in response to the drive signal having the same frequency as the first natural frequency. That is, the pixel P superimposed by the ultrasonic generator 390 operating in the pull-in mode may function as an inactive pixel, which does not generate unit-ultrasonic waves.

In the case where the bias voltage Bias (V) is decreased to the pull-out voltage Vpo from the pull-in voltage Vpi when the ultrasonic generator 390 is operating in the pull-in mode, the operation mode of the ultrasonic generator 390 may be changed to the normal mode. Accordingly, the ultrasonic generator 390 may operate based on the drive signal having the same frequency as the first natural frequency.

The bias voltage Bias (V) may be applied to the CMUT device CM via the signal line 200. The CMUT device CM may function as a capacitor having the capacitance C0(pF) corresponding to the bias voltage Bias (V). When the drive signal, which is an AC signal, is applied to the CMUT device CM, the membrane 320 may vibrate to generate ultrasonic waves. Specifically, if the frequency of the drive signal is identical to the natural frequency of the CMUT device CM, the CMUT device CM may resonate to generate unit-ultrasonic waves. The bias voltage may be determined such that the CMUT device CM has a proper capacitance for allowing the membrane 320 to vibrate.

In the case where the bias voltage smaller than the pull-in voltage Vpi is applied to the ultrasonic generator 390, the ultrasonic generator 390 may operate in the normal mode. Moreover, the pixel P corresponding to the ultrasonic generator 390 operating in the normal mode may function as an active pixel, which is capable of generating ultrasonic waves.

As described above, based on the bias voltage, the operation mode of the ultrasonic generator 390 may be converted from one of the normal mode and the pull-in mode to the other of the normal mode and the pull-in mode.

When the bias voltage increases to the pull-in voltage, the operation mode of the ultrasonic generator 390 may be changed to the pull-in mode. Then, when the bias voltage decreases again to become smaller than the pull-out voltage Vpo, the balance between the restitution of the membrane 320 and the electrostatic force of electrostatic charge may be restored to change the operation mode of the ultrasonic generator back to the normal mode.

When the operation mode of the ultrasonic generator is changed to the pull-in mode, there may be a static friction force between the membrane 320 and the insulation film 310 of the ultrasonic generator 390. In other words, in order to recover the original shape of the membrane 320 and change the operation mode of the ultrasonic generator back to the normal mode, the difference between the bias voltage and the pull-in voltage Vpi needs to be sufficient enough to overcome the aforementioned static friction force. In the case where the difference between the bias voltage and the pull-in voltage Vpi is not sufficient enough to overcome the static friction force, the operation mode of the ultrasonic generator 390 may be maintained in the pull-in mode.

With respect to a predetermined bias voltage, the capacitance C0(pF) of the CMUT device CM of the ultrasonic generator may vary based on one of the pull-in path Ppi and the pull-out path Ppo. Specifically, although the same bias voltage Bias (V) is applied to the ultrasonic generator, the capacitance C0(pF) of the CMUT device CM may vary based on the pull-out path Ppo if the operation mode of the ultrasonic generator is the pull-in mode, and the capacitance C0(pF) of the CMUT device CM may vary based on the pull-in path Ppi if the operation mode of the ultrasonic generator is the normal mode.

While the operation mode of the ultrasonic generator is the pull-in mode and the bias voltage Bias (V) is decreasing (Ppo) to the pull-out voltage Vpo, the capacitance C0(pF) of the CMUT device CM of the ultrasonic generator corresponding to the predetermined bias voltage may be a first value.

While the operation mode of the ultrasonic generator is the normal mode and the bias voltage Bias (V) is increasing (Ppo) to the pull-in voltage Vpi, the capacitance C0(pF) of the CMUT device CM of the ultrasonic generator corresponding to the predetermined bias voltage may be a second value.

The first value may be greater than the second value. In other words, the capacitance C0(pF) of the CMUT device CM of the ultrasonic generator may be greater when the operation mode of the ultrasonic generator is the pull-in mode than when the operation mode of the ultrasonic generator is the normal mode.

In the case where the bias voltage becomes smaller than or equal to the pull-out voltage Vpo, the membrane 320 may overcome the static friction force and be separated from the insulation film 310. That is, the pull-out voltage Vpo may be a voltage for restoring the operation mode of the CMUT device CM to the normal state.

In the present specification, a primary bias voltage means a bias voltage having a tendency of increasing from a voltage that is smaller than the pull-out voltage Vpo to a voltage that is greater than the pull-out voltage Vpo.

In the case where the bias voltage becomes smaller than the pull-in voltage Vpi, the operation mode of the ultrasonic generator 390 may be maintained in the pull-in mode until the pull-out voltage Vpo is reached. Moreover, the capacitance C0(pF) of the CMUT device CM may vary based on the pull-out path Ppo. That is, the operation mode of the ultrasonic generators 390 may be determined according to the primary bias voltage and the secondary bias voltage.

Figure 5B:
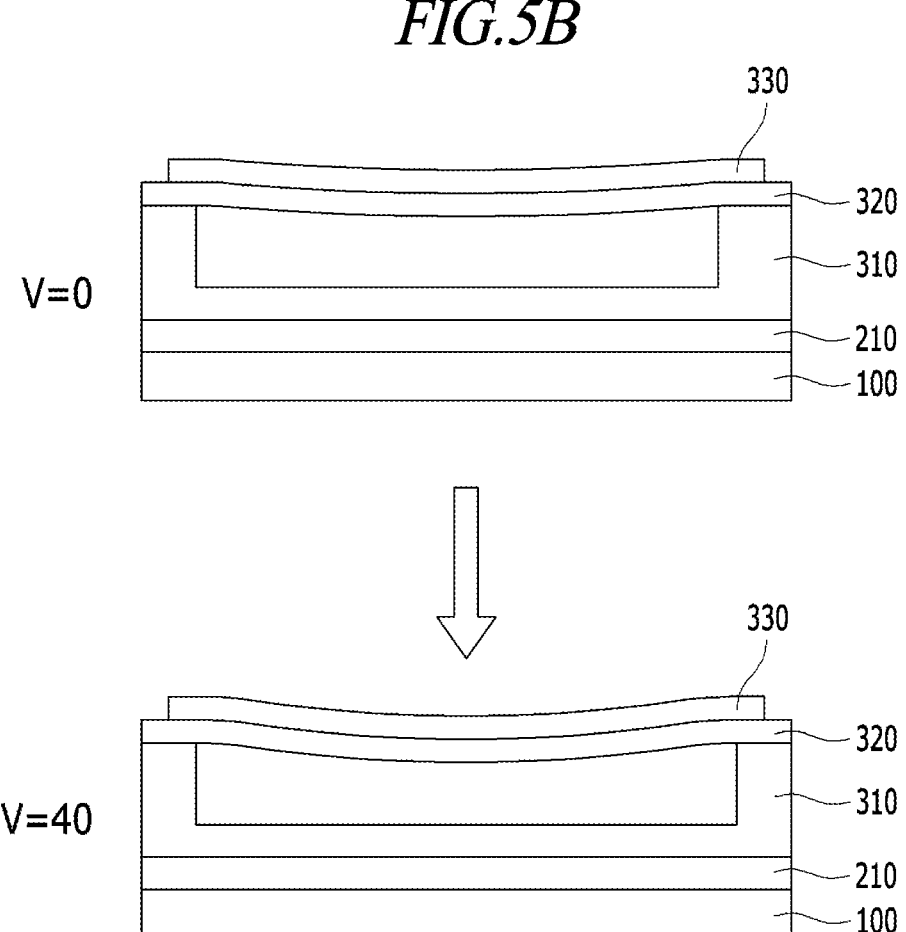
FIG. 5B and FIG. 5C illustrate the operation of the ultrasonic generator according to the same magnitude of primary bias voltage and secondary bias voltage.
Figure 5C:
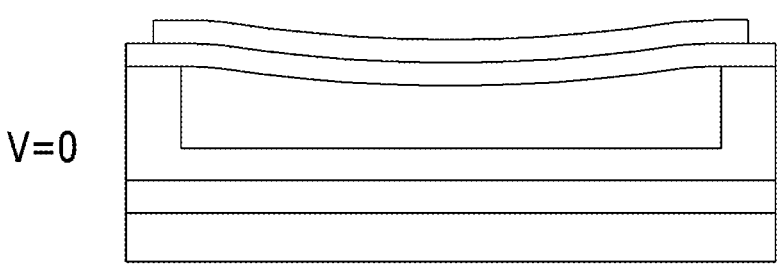
Figure 5C:
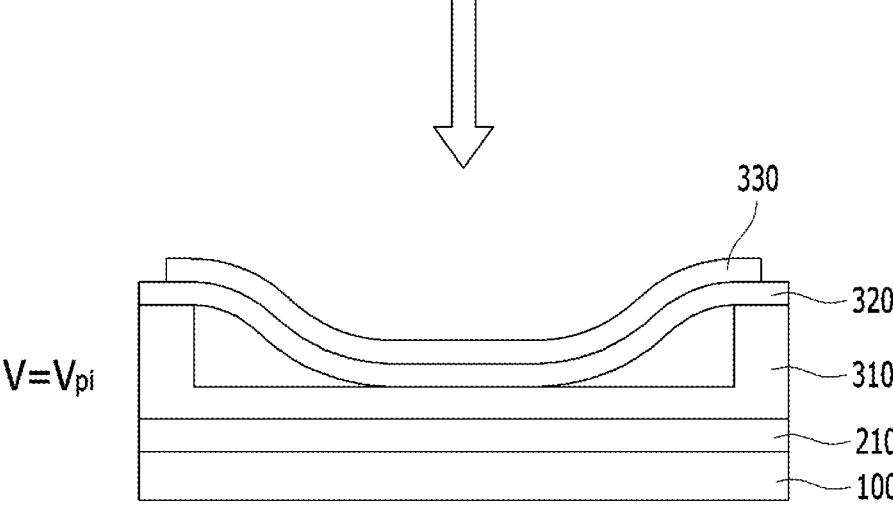
Figure 5C:
Figure 5C:
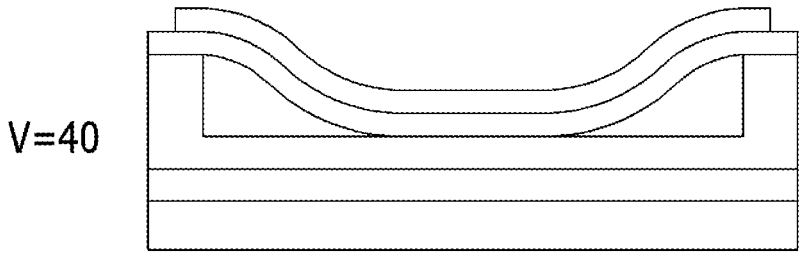

FIG. 5B and FIG. 5C illustrate the operation of the ultrasonic generator according to the same magnitude of primary bias voltage and secondary bias voltage.

In FIGS. 5B and 5C, the pull-in voltage of the ultrasonic generator may be 50 V, and the pull-out voltage of the ultrasonic generator may be 35 V. Hereinafter, the operation mode of the ultrasonic generator will be described when the primary bias voltage and the secondary bias voltage are both 40 V.

Referring to FIG. 5B, when the bias voltage increases to be greater than the pull-out voltage Vpo and smaller than the pull-in voltage Vpi, the operation mode of the ultrasonic generator 390 may be maintained in the normal mode.

In the present specification, a primary bias voltage means a bias voltage having a tendency of increasing from a voltage that is smaller than the pull-out voltage Vpo to a voltage that is greater than the pull-out voltage Vpo.

In the present specification, a secondary bias voltage means a bias voltage having a tendency of decreasing from a voltage that is greater than the pull-in voltage Vpi to a voltage that is smaller than the pull-in voltage Vpi.

Referring to FIG. 5C, when the secondary bias voltage that is greater than the pull-out voltage Vpo and smaller than the pull-in voltage Vpi is applied, the operation mode of the ultrasonic generator 390 may be maintained in the pull-in mode.

In short, even though the bias voltage is the same magnitude, the operation mode of the ultrasonic generator 390 may vary depending on whether the bias voltage is a primary bias voltage or a secondary bias voltage.

That is, even if the bias voltage applied to the ultrasonic generator 390 operating in the pull-in mode becomes smaller than the pull-in voltage Vpi, the operation mode of the ultrasonic generator 390 may be maintained in the pull-in mode if the bias voltage applied to the ultrasonic generator 390 is a secondary bias voltage.

In other words, as long as the bias voltage is properly adjusted, the operation mode of the ultrasonic generator 390 may be maintained even if at least one of the mode voltage and the scan voltage is changed. The operation mode of the ultrasonic generator 390 may correspond to data stored in the pixel.

Figure 6:
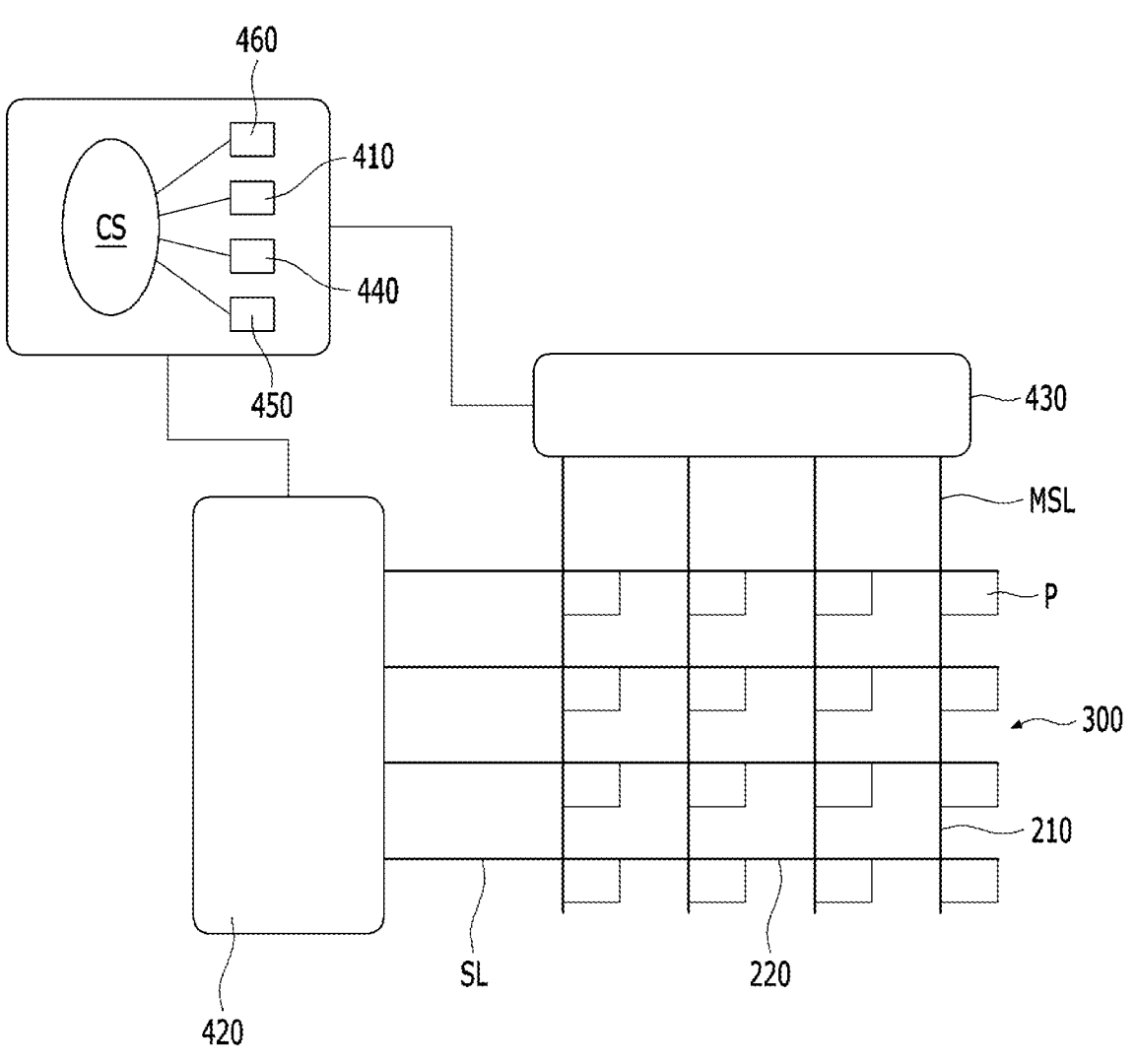
FIG. 6 illustrates an exemplary configuration of a pixel coder in accordance with an embodiment of the present disclosure.

FIG. 6 illustrates an exemplary configuration of a pixel coder in accordance with an embodiment of the present disclosure.

Referring to FIG. 6, the pixel coder 400 may include an initialization driver 410, a scanline setter 420, a mode line setter 430, a pull-in coder 440, a timing controller 450, a pixel reset unit 460 and a coding control center CS.

The pixel coder 400 may be configured to generate the coding array 301 by coding each of the plurality of pixels P of the ultrasonic array 300 so that a operation mode of each of the plurality of pixels P may be a contrasting binary operation mode of the ultrasonic generator 390. The term "binary operation mode," as used in the present specification, may be interpreted as meaning that the operation mode may be determined as one of the normal mode and the pull-in mode. The binary operation mode of the ultrasonic generator 390 may be one of the normal mode and the pull-in mode. The coding array 301 may include an active pixel and an inactive pixel.

The scanline setter 420 may electrically connected selectively with at least one of the plurality of second conductive lines 220. That is, the scanline setter 420 may be short-circuited or opened to each of the plurality of second conductive lines 220 according to a control signal received from the coding control center CS. Similarly, the mode line setter 430 may electrically connected selectively with at least one of the plurality of first conductive lines 210. The mode line setter 430 may be short-circuited or opened to each of the plurality of first conductive lines 210 according to the control signal received from the coding control center CS.

The initialization driver 410, the pull-in coder 440, the timing controller 450 and the pixel reset unit 460 may each receive the control signal generated by the coding control center CS and transmit electrical signals to the first conductive lines 210 and the second conductive lines 220 through the scanline setter 420 and the mode line setter 430.

The initialization driver 410 may be configured to apply an initialization signal to the first conductive lines 210 and the second conductive lines 220 to initialize the operation mode of the ultrasonic generators 390 to the normal mode.

When a coding start signal is applied to the coding control center CS, the coding control center CS may control the initialization driver 410 to apply the initialization signal to the signal line 200.

The initialization driver 410 may be configured to apply the initialization signal to the first conductive lines 210 and the second conductive lines 220. The initialization signal may include a first partial setting signal and a second partial setting signal. The first partial setting signal may be simultaneously applied to the plurality of first conductive lines 210. The second partial setting signal may be simultaneously applied to the plurality of second conductive lines 220.

A setting voltage Vs may be the potential difference between the first partial setting voltage Vs1 of the first partial setting signal and the second partial setting voltage Vs2 of the second partial setting signal. The setting voltage Vs may be a primary bias voltage satisfying the condition expressed in (1) below. The setting voltage Vs may be simultaneously applied to the plurality of ultrasonic generators 390.

$$Vpo < Vs = (Vs1 - Vs2) < Vpi \qquad (1)$$

In condition (1), Vpo may be the pull-out voltage, and Vpi may be the pull-in voltage. Vs may be the setting voltage, whereas Vs1 may be the first partial setting voltage, and Vs2 may be the second partial setting voltage.

Referring to condition (1), since the setting voltage Vs that is lower than the pull-in voltage Vpi is applied to the ultrasonic generator 390 as the primary bias voltage, the operation mode of the ultrasonic generator 390 may be set as the normal mode. In other words, the operation mode of the ultrasonic generators to which the initialization signal is applied may be the normal mode.

Once the initialization is complete for the ultrasonic array 300, the coding control center CS may transmit a pull-in coding signal to the timing controller 450. Based on the pull-in coding signal, the timing controller 450 may control the scanline setter 420, the mode line setter 430 and the pull-in coder 440 to code some of the plurality of pixels P, coded with the normal mode, with the pull-in mode.

The scanline setter 420 may be configured to select one of the second conductive lines 220 as a scan line SL for transmitting the scan signal. The scanline setter 420 may be configured to select the pixel row PR of the ultrasonic array 300 corresponding to the scan line SL as a coding row.

In an embodiment of the present disclosure, the second conductive lines 220 may be successively selected one by one along a predetermined direction as the scan line SL. That is, all of the second conductive lines 200 may be selected one by one successively as the scan line SL. The plurality of pixels corresponding to the scan line SL may be selected as a coding row CR (see FIG. 7).

FIG. 7 illustrates an exemplary generation of amplitude-modulated ultrasonic waves AMU from the coding array 301.

Referring to FIG. 7, the mode line setter 430 may be configured to select at least one of the plurality of first conductive lines 210 as a mode changing line MSL. The mode changing line MSL may be a first conductive line for transmitting the mode changing signal. The mode changing signal may convert the operation mode of the ultrasonic generator superimposed on a pixel P. The mode line setter 430 may be configured to select a pixel column corresponding to the mode changing line MSL as a coding column.

Information about the pixel column including a coding target pixel, among the pixels of the coding row selected by the timing controller 450, may be transmitted to the mode line setter 430. The mode line setter 430 may be configured to select the first conductive line 210 of the plurality of first conductive lines 210 that corresponds to the pixel column as the mode changing line MSL. The plurality of pixels corresponding to the mode changing line MSL may be set as a single coding column CC (see FIG. 7).

Once the scan line SL and the mode changing line MSL are selected, the pull-in coder 440 may apply the scan signal and the mode changing signal to the scan line SL and the mode changing line MSL, respectively. A scan voltage may be the voltage of the scan signal. A mode voltage may be the voltage of the mode changing signal.

The coding target pixel may be a pixel where the coding row and the coding column intersect. The operation mode of the ultrasonic generator 390 superimposed on the coding target pixel may be changed to the pull-in mode by the bias voltage that is higher than the pull-in voltage Vpi. The bias voltage applied to the ultrasonic generator 390 may be a potential difference between the mode voltage and the scan voltage Vscan. That is, the pull-in coder 440 may be configured to perform a pull-in coding operation, in which a pixel P coded in the normal mode is coded in the pull-in mode.

In an embodiment of the present disclosure, when the mode voltage Vmode and the scan voltage satisfy the below conditions (2) to (4), a bias voltage that is greater than the pull-in voltage Vpi may be applied to the ultrasonic generator superimposed on the coding target pixel. That is, the operation mode of the ultrasonic generator superimposed on the coding target pixel among the ultrasonic generators superimposed on the coding row may be changed to the pull-in mode. On the other hand, the operation mode of the ultrasonic generator not corresponding to the coding target pixel among the ultrasonic generators superimposed on the coding row may be kept in the normal mode.

$$Vs - Vscan < Vpi \qquad (2)$$
$$Vmode - Vscan > Vpi \qquad (3)$$
$$Vmode < Vpi \qquad (4)$$

In conditions (2) and (4), Vs may be a setting voltage, and Vscan may be a scan voltage, and Vmode may be a mode voltage.

Once the pull-in coding operation is complete for the selected coding row CR and coding column CC, a next pixel row PR may be selected by the timing controller 450 as a new coding row. Moreover, among the pixels included in the new coding row, a pixel column including the coding target pixel may be selected as a new coding column by the timing controller 450. Accordingly, the second conductive line and the first conductive line corresponding to the new coding row and the new coding column may be selected as a new scan line SL and a new mode changing line MSL, respectively.

Then, the scan voltage and the mode voltage may be applied, respectively, to the new scan line SL and the new mode changing line MSL. Accordingly, the operation mode of the ultrasonic generator corresponding to the new coding target pixel may be set to the pull-in mode.

The timing controller 450 may be configured to successively select the plurality of pixel rows one by one and then selectively perform the pull-in coding operation for some of the pixels belonging to the pixel row. Accordingly, every pixel P of the ultrasonic array 300 may be coded to have data corresponding to one of the normal mode and the pull-in mode.

Here, the operation mode of the pull-in pixel that has been already coded in the pull-in mode in the previous coding row CR while the pull-in coding operation is performed for the selected coding row CR may be maintained without changing.

The scan voltage Vscan and the mode voltage Vmode set in the pull-in coding operation for the previous coding row may not be maintained in the pull-in coding operation for another coding row that is selected later. Therefore, the operation mode of the pull-in pixel may be maintained, regardless of the change of the bias voltage for the pull-in pixel.

In an embodiment of the present disclosure, when the scan voltage Vscan, the mode voltage Vmode and the setting voltage Vs satisfy the below condition (5), the operation mode of the pull-in pixel that has been already coded in the pull-in mode may be maintained.

$$\mathrm{V}po < \mathrm{V}\,mode < \mathrm{V}pi \quad (5)$$

Based on the setting voltage, scan voltage and mode voltage satisfying the above condition, the pixel P coded in the normal mode may be coded in the pull-in mode. Accordingly, generated is a coding array 301 that includes active pixels AP coded in the normal mode and inactive pixels IAP coded in the pull-in mode based on the ultrasonic array 300.

For instance, in the case where the pull-in voltage of the CMUT device of the ultrasonic generator 390 is 50 V and the pull-out voltage is 30 V, the pixel P may be coded in the pull-in mode if the setting voltage, the scan voltage and the mode voltage are, respectively, 35 V, −10 V and 45 V. However, this is merely an example, and it shall be appreciated that the setting voltage, the scan voltage and the mode voltage of the present disclosure are not limited to the described example.

In the present specification, a pixel map may refer to information relating to the distribution of the active pixels AP and inactive pixels IAP of the coding array 301. The coding control center CS may be configured to control the pixel reset unit 460 to reset the active pixels AP and inactive pixels IAP of the coding array 301. After the active pixels AP and inactive pixels IAP of the coding array 301 are reset, the pixel map may be changed.

When a pixel reset signal is detected, the pixel reset unit 460 may control the scanline setter 420 and the mode line setter 430 to ground the signal line 200. Accordingly, the active pixels AP and the inactive pixels IAP of the coding array 301 may be reset to a pre-coding state. Thereafter, a coding array corresponding to the changed pixel map may be generated.

In an embodiment of the present disclosure, the ultrasonic driver 500 may be configured to drive the coding array 301. The coding array 301 may generate amplitude-modulated ultrasonic waves AMU. The wavefront of the amplitude-modulated ultrasonic waves AMU may be deformed. The amplitude-modulated ultrasonic waves AMU may be a synthesis of a plurality of unit-ultrasonic waves generated by the plurality of ultrasonic generators. Each of the plurality of ultrasonic generators may be superimposed on an active pixel AP.

In an embodiment of the present disclosure, the ultrasonic driver 500 may include a drive setting unit 510 and a driving unit 520.

The drive setting unit 510 may be configured to apply a drive-bias to the coding array 301 to control the bias voltages applied to the plurality of ultrasonic generators of the coding array 301 to be identical with each other.

Since the scan voltage Vscan and the mode voltage Vmode are simultaneously applied to the plurality of ultrasonic generators corresponding to the coding column CC, the bias voltages applied to the plurality of ultrasonic generators may be different from each other. When the bias voltages applied to the plurality of ultrasonic generators are different from each other, the intensities of the ultrasonic waves generated at the plurality of active pixels corresponding to the plurality of ultrasonic generators may be different from each other. Accordingly, the wavefront of the amplitude-modulated ultrasonic waves may be distorted.

The drive setting unit 510 may be configured to apply a drive-bias satisfying condition (6) described below to the first conductive lines 210 and control the second conductive lines 220 to be grounded.

$$\mathrm{V}po < \mathrm{V}d < \mathrm{V}pi \quad (6)$$

Vpo may be a pull-out voltage, and Vpi may be a pull-in voltage. Vd may be a drive-bias.

That is, if the drive-bias is smaller than the pull-in voltage and greater than the pull-out voltage, the operation mode of the ultrasonic generator corresponding to the pull-in pixel may be maintained in the pull-in mode.

The driving unit 520 may be configured to apply an AC drive signal to the coding array 301 and control the ultrasonic waves to be generated at an active pixel AP. By successively applying the drive-bias and the drive signal to the ultrasonic generator corresponding to the active pixel AP, the electrostatic charge accumulated in the CMUT device CM of the ultrasonic generator may vibrate to generate ultrasonic waves.

The frequency of the AC signal may be the same as the first natural frequency. The first natural frequency may be the natural frequency of the CMUT device CM operating in the normal mode. The first natural frequency may be different from the second natural frequency, which is the natural frequency of the CMUT device CM of the ultrasonic generator operating in the pull-in mode. Therefore, the CMUT device CM of the ultrasonic generator of which the operation mode is the pull-in mode may not be operated by the drive signal.

That is, while ultrasonic waves having the largest acoustic energy are generated in response to the drive signal at the active pixels corresponding to the ultrasonic generator of which the operation mode is the normal mode, the ultrasonic waves may be hardly generated at the inactive pixels corresponding to the ultrasonic generator of which the operation mode is the pull-in mode.

The amplitude-modulated ultrasonic waves AMU may be generated by synthesizing the plurality of unit-ultrasonic waves generated at the plurality of active pixels AP of the coding array 301.

Referring to FIG. 7, once the drive signal is applied, the coding array 301 may generate the amplitude-modulated ultrasonic waves in which the wavefront may be shaped correspondingly to the pixel map.

When the operation mode of the ultrasonic generator corresponding to the pixel is the normal mode, the pixel may function as the active pixel AP. The unit-ultrasonic waves may be generated at the active pixel AP in response to the AC drive signal.

When the operation mode of the ultrasonic generator corresponding to the pixel is the pull-in mode, the pixel may function as the inactive pixel IAP. The unit-ultrasonic waves may not be generated at the inactive pixels IAP in response to the AC drive signal.

The active pixel AP may be a point source of the unit-ultrasonic wave, which is a spherical wave. That is, the coding array 301 may include a plurality of point sources that correspond to the pixel map and configured to generate a plurality of unit-ultrasonic waves. The sound pressure of each of the plurality of CMUT devices may be generated in the form of unit-ultrasonic waves.

The wavefront of the amplitude-modulated ultrasonic waves AMU may be determined by the distribution of sound pressure. The wavefront of the amplitude-modulated ultrasonic waves AMU may be shaped to bend downwardly around the inactive pixels IAP and to bend upwardly around the active pixels AP. Accordingly, the coding array 301 may generate the amplitude-modulated ultrasonic waves AMU corresponding to the pixel map.

The shape of the wavefront of the amplitude-modulated ultrasonic waves AMU may be determined by the pixel map. Specifically, the operation mode of the ultrasonic generator 390 may be changed according to the scan voltage Vscan, the mode voltage Vmode and the setting voltage Vs. Moreover, the pixel map may be changed in real time according to the scan signal and the mode changing signal. Therefore, a plurality of amplitude-modulated ultrasonic waves AMU having different shapes of wavefront according to the scan signal and the mode changing signal may be generated.

For example, the waveform controller 600 may be configured to control the pixel coder 400 to change the coding array 301 according to the wavefront information. Moreover, the waveform controller 600 may control the ultrasonic driver to generate amplitude-modulated ultrasonic waves according to the changed coding array 301. If the coding array 301 is continuously changed, the wavefront of the amplitude-modulated ultrasonic waves may be also continuously changed. That is, the present disclosure may allow the user to generate the amplitude-modulated ultrasonic waves of which the wavefront is continuously changed with time.

Figure 8:
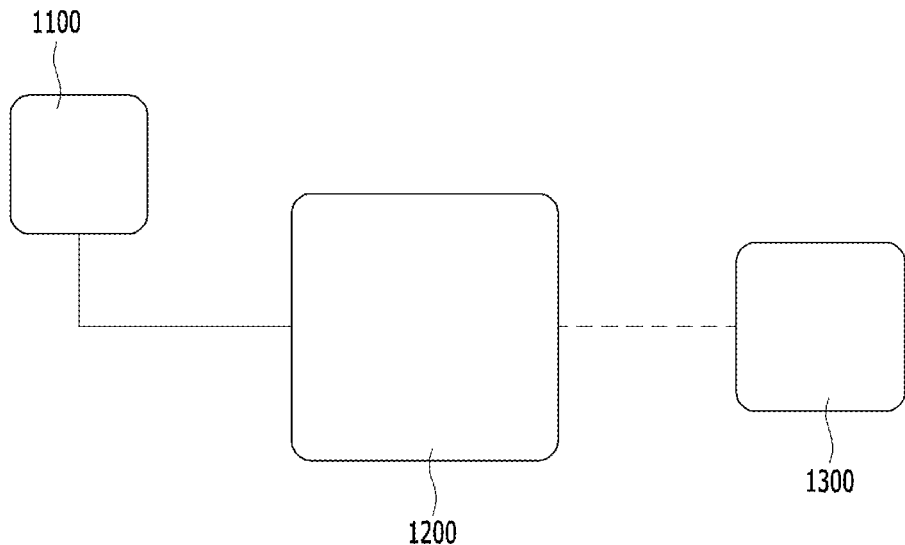
FIG. 8 illustrates an exemplary configuration of an ultrasonic apparatus in accordance with an embodiment of the present disclosure.

FIG. 8 illustrates an exemplary configuration of an ultrasonic apparatus 2000 in accordance with an embodiment of the present disclosure.

In the ultrasonic apparatus in accordance with an embodiment of the present disclosure, the amplitude-modulated ultrasonic waves generated by the spatial ultrasound modulator 1200 may be used as incident waves for ultrasonic processing of a target object. The spatial ultrasound modulator 1200 is substantially the same as the spatial ultrasound modulator 1000 described with reference to FIGS. 1 to 7. Hereinafter, the spatial ultrasound modulator 1200 will be described with reference to the drawing symbols used in FIGS. 1 to 7.

Referring to FIG. 8, the ultrasonic apparatus 2000 in accordance with an embodiment of the present disclosure may include a wavefront information setter 1100, a spatial ultrasound modulator 1200 and a response detection unit 1300.

The wavefront information setter 110 may be configured to set wavefront information corresponding to incident waves, which are spatially modulated ultrasonic waves incident on a target object.

The spatial ultrasound modulator 1200 may generate a coding array 301 based on the wavefront information. The spatial ultrasound modulator 1200 may generate amplitude-modulated ultrasonic waves having the wavefront corresponding to the wavefront information. The amplitude-modulated ultrasonic waves generated by the spatial ultrasound modulator 1200 may be used as incident waves.

The response detection unit 1300 may be configured to detect a response of the target object for ultrasonic processing to the incident waves.

The wavefront information setter 1100 may be configured to generate a pixel map corresponding to the wavefront information. The wavefront information may be inputted in real time by the user. Moreover, the wavefront information may be included in a pre-stored database. The pixel map may be modified according to the shape of the target object, the characteristics of the target object and the purpose of ultrasonic processing.

In an embodiment of the present disclosure, the wavefront information setter 1100 may include a data storage and an array setter.

The data storage may be configured to store reference data. The reference data may include a plurality of pixel maps and matching information between wavefronts of a plurality of reference amplitude-modulated ultrasonic waves. The wavefront of each of the plurality of reference amplitude-modulated ultrasonic waves may correspond to one of the plurality of pixel maps. Moreover, each of the plurality of reference amplitude-modulated ultrasonic waves may be amplitude-modulated ultrasonic waves generated by a sample array.

The array setter may be configured to select one of a plurality of sample arrays as a set array. The set array may be a sample array of the plurality of sample arrays that corresponds to the shape of wavefront of the reference amplitude-modulated ultrasonic waves corresponding to the incident waves.

The data storage may be configured to store pixel-wavefront matching information with respect to the pixel map of the sample array and the wavefront of the reference amplitude-modulated ultrasonic waves.

The pixel-wavefront matching information may include information about troughs and peaks of the reference amplitude-modulated ultrasonic waves and the separation distance between the plurality of pixels constituting the sample array.

Based on the pixel-wavefront matching information, the distribution of the operation modes of a plurality of ultrasonic generators of the set array. The set array may be transferred to the coding control center CS.

Accordingly, the coding array 301 corresponding to the set array may be generated. By having a drive signal applied to the coding array 301, amplitude-modulated ultrasonic waves having a predetermined wavefront shape may be generated.

As mentioned, the spatial ultrasound modulator 1200 configured for generating amplitude-modulated ultrasonic waves AMU has substantially identical configurations as the spatial ultrasound modulator 1000 illustrated in FIG. 1 and thus will not be redundantly described.

The spatial ultrasound modulator 1200 may be couple to a housing configured with a flexible material. The spatial ultrasound modulator 1200 may modify the coding array according to the shape of the target object. By adjusting the shape of the housing to correspond to the shape and curvature of the target object, the incident waves generated by the spatial ultrasound modulator 1200 may be readily focused at the target object.

For example, the target object may be an object for testing for an imaging of internal defect or shape using amplitude-modulated ultrasonic waves. Moreover, the target object may be a living body in which nerves stimulated by the amplitude-modulated ultrasonic waves are arranged. In other words, the ultrasonic apparatus 2000 of the present disclosure may be used as an ultrasonic inspection apparatus and ultrasonic neural stimulation apparatus.

The response detection unit 1300 may be adapted according to the characteristics of the target object. For example, if the target object is a living body arranged with nerves stimulated by the amplitude-modulated ultrasonic waves, the response detection unit 1300 may be a device for detecting and storing operational characteristics, including at least one of the form, periodicity and magnitude of the response. Moreover, the response detection unit 1300 may be a device for comparing the operation and condition before and after neural stimulation by the amplitude-modulated ultrasonic waves.

For instance, the response detection unit 1300 may be a device for detecting a biological signal generated in response to the amplitude-modulated ultrasonic waves in a living body in which nerves are arranged. If the biological signal is an electrical signal, the response detection unit 1300 may be a device capable of detecting at least one of voltage and current. If the biological signal is a chemical substance including hormones, the response detection unit 1300 may be a device capable of detecting the composition and concentration of the chemical substance.

In an embodiment of the present disclosure, the response detection unit 1300 may not be coupled with the spatial ultrasound modulator 1200 but arranged to be separated from the spatial ultrasound modulator 1200. Specifically, if the response detection unit 1300 is a device for detecting and storing the operational characteristics, the response detection unit 1300 may not be coupled with the spatial ultrasound modulator 1200 but arranged to be separated from the spatial ultrasound modulator 1200.

On the other hand, if the response detection unit 1300 is a device for detecting electrical or chemical signals, the response detection unit 1300 may be connected with the spatial ultrasound modulator 1200 to be linked to the ultrasonic characteristics and analyze the detected signals.

In an embodiment of the present disclosure, the response detection unit 1300 may be coupled and electrically connected to the spatial ultrasound modulator 1200. Specifically, in the case where the response detection unit 1300 is a device for comparing the operation and condition before and after neural stimulation by the amplitude-modulated ultrasonic waves, the response detection unit 1300 may be electrically connected to the spatial ultrasound modulator 1200. Moreover, the response detection unit 1300 may be configured to analyze the biological signal based on the characteristics of the amplitude-modulated ultrasonic waves generated by the spatial ultrasound modulator 1200.

In an embodiment of the present disclosure, if the target object is an object for testing for an internal defect or shape using amplitude-modulated ultrasonic waves, the response detection unit 1300 may perform the function of detecting reflected waves generated inside the target object in response to the amplitude-modulated ultrasonic waves. The response detection unit 1300 may be a device for collecting information about the inside of the target object using the reflected waves.

For example, the reflected waves generated inside the target object in response to the amplitude-modulated ultrasonic waves may be detected by the plurality of CMUT devices CM of the spatial ultrasound modulator. The reflected waves detected by the plurality of CMUT devices CM may be used for collecting the information about the inside of the target object. As the integration density of the CMUT device CM increases, the focusing resolution for the reflected waves generated inside the target object may be improved, and the information about the inside of the target object may be collected more accurately.

Specifically, in the course of generating amplitude-modulated ultrasonic waves, which are incident waves, the ultrasonic generator 390 may convert electrical energy to acoustical energy, i.e., ultrasonic waves. By contrast, in the course of detecting reflected waves, the ultrasonic generator 390 may convert the acoustical energy of the reflected waves to electrical energy. In other words, if the integration density of the CMUT device CM is increased, not only the focusing resolution but also the detection resolution of the reflected waves may be improved.

With the present disclosure, by modifying the coding array 301 by adjusting the setting voltage, scan voltage and mode voltage, the wavefront of the incident waves being incident at the target object may be deformed in real time.

FIGS. 9A to 9F illustrate a method of generating amplitude-modulated ultrasonic waves.

Hereinafter, the method of generating amplitude-modulated ultrasonic waves of FIGS. 9A to 9F will be described with reference to the drawing symbols used in FIGS. 1 to 9.

Figures 9A, 9B:
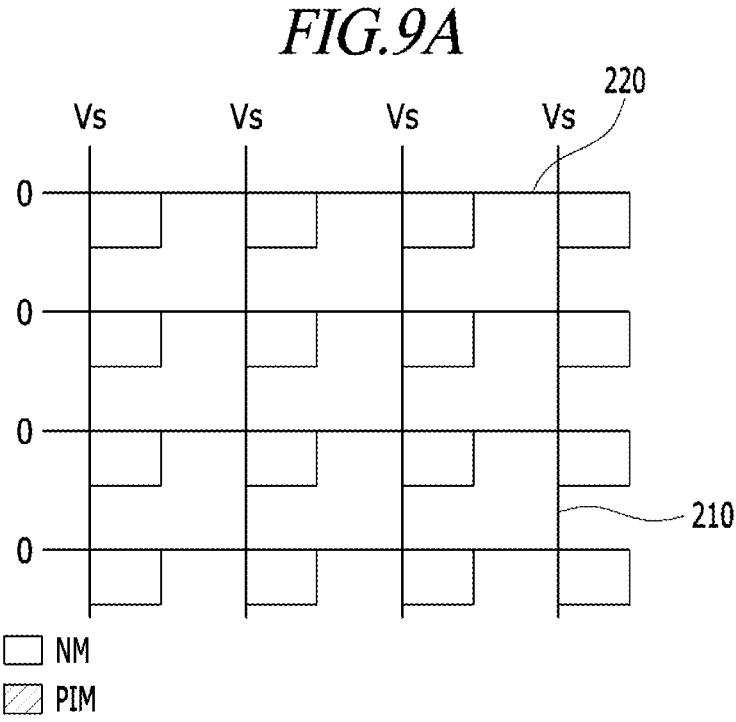
FIGS. 9A to 9F illustrate a method of generating amplitude-modulated ultrasonic waves.

Referring to FIG. 9A, the method of generating amplitude-modulated ultrasonic waves in accordance with an embodiment of the present disclosure may include step 1, step 2, step 3 and step 4.

In step 1, an ultrasonic array may be initialized to a setting voltage Vs, and the operation mode of a plurality of ultrasonic generators may be changed to a normal mode NM. The ultrasonic array may include a plurality of pixel rows and a plurality of pixel columns. Each pixel row PR and pixel column PC may include a plurality of ultrasonic generators. Each of the plurality of ultrasonic generators may be superimposed on one of the plurality of pixels.

Specifically, a first partial setting signal having a first partial setting voltage may be applied to a first conductive line 210. A second partial setting signal having a second partial setting voltage may be applied to a second conductive line 220. A setting voltage Vs may be the potential difference between the first partial setting voltage Vs1 of the first partial setting signal and the second partial setting voltage Vs2 of the second partial setting signal. The setting voltage Vs may be applied to the ultrasonic generator 390.

In an embodiment of the present disclosure, a second conductive line 220 may be grounded, and the setting voltage Vs may be the first partial setting voltage Vs1. In order to change the operation mode of the ultrasonic generator to the normal mode NM, the setting voltage Vs may be determined with a value between a pull-out voltage and a pull-in voltage.

In step 2, the pixel rows may be successively selected one by one as a coding row. Moreover, at least one of the plurality of pixel columns corresponding to a coding target pixel may be selected as a coding column.

Referring to FIG. 9B, in step 3, the operation mode of the ultrasonic generator corresponding to the coding target pixel may be changed to a pull-in mode to generate a coding array. The coding array may include an active pixel and an inactive pixel. An active pixel may be a pixel of which the operation mode of the corresponding ultrasonic generator is coded in the normal mode. An inactive pixel may be a pixel of which the operation mode of the corresponding ultrasonic generator is coded in the pull-in mode. A coding target pixel may be a pixel arranged at an intersection of the coding row and the coding column.

A first natural frequency may be different from a second natural frequency. The first natural frequency may be a natural frequency of the ultrasonic generator of which the operation mode is the pull-in mode. The second natural frequency may be a natural frequency of the ultrasonic generator of which the operation mode is the normal mode. Whenever a coding row is selected, a scan voltage and a mode voltage may be applied to the coding row and the coding column, and the operation mode of the ultrasonic generator corresponding to the coding target pixel may be changed to the pull-in mode.

Referring to FIG. 9B, the scan voltage Vscan may be applied to one of the plurality of first conductive lines 210, and a first pixel row PR1 may be selected as the coding row. Then, among the plurality of first conductive lines 210, a third first conductive line and a fourth first conductive line may be selected to mode changing lines MSL. The mode voltage Vmode may be applied to the mode changing lines MSL. The operation mode of the ultrasonic generators superimposed on the third pixel P13 and the fourth pixel P14 of the first pixel row PR1 may be changed to the pull-in mode PIM.

According to an embodiment of the present disclosure, in step 3, if the setting voltage Vs, the scan voltage Vscan and the mode voltage Vmode satisfy the below conditions (2) to (4), the operation mode of the ultrasonic generator that is not superimposed on the coding target pixel among the plurality of ultrasonic generators superimposed on the coding row may be maintained in the normal mode NM.

Referring to FIG. 9B, a bias voltage greater than the pull-in voltage Vpi may be applied to the ultrasonic generators superimposed on the third pixel P13 and the fourth pixel P14 of the first pixel row PR1. Accordingly, the operation mode of the pertinent ultrasonic generators may be changed from the normal mode NM to the pull-in mode PIM.

On the other hand, a bias voltage smaller than the pull-in voltage Vpi may be applied to the ultrasonic generators superimposed on the first pixel P11 and the second pixel P12 of the first pixel row PR1. Accordingly, the operation mode of the pertinent ultrasonic generators may be maintained in the normal mode NM.

$$Vs - Vscan < Vpi \tag{2}$$

$$Vmode - Vscan > Vpi \tag{3}$$

$$Vmode < Vpi \tag{4}$$

In conditions (2) and (4), Vs may be the setting voltage. Vscan may be the scan voltage, and the Vmode may be the mode voltage.

Figure 9C:
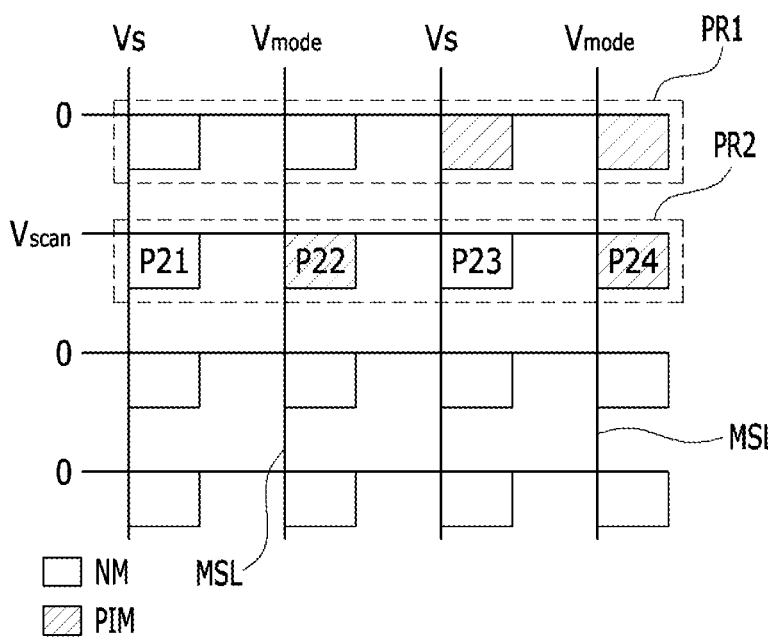

Referring to FIG. 9C, the first pixel row PR1 may be grounded. Then, by having the scan voltage Vscan applied to the first conductive line, the second pixel row PR2 may be selected as the coding row. Then, in order to change the operation mode of the ultrasonic generators superimposed on the second pixel P22 and the fourth pixel P24 of the second pixel row PR2 to the pull-in mode, the second first conductive line and the fourth first conductive line of the plurality of first conductive lines 210 may be selected as the mode changing lines MSL. The mode voltage Vmode may be applied to the second first conductive line and the fourth first conductive line of the plurality of first conductive lines 210.

Here, if the scan voltage Vscan, the mode voltage Vmode and the setting voltage Vs satisfy conditions (2) and (3), a bias voltage greater than the pull-in voltage may be applied to the ultrasonic generators superimposed on the second pixel P22 and the fourth pixel P24 of the second pixel row PR2. Accordingly, the operation mode of the ultrasonic generators superimposed on the second pixel P22 and the fourth pixel P24 of the second pixel row PR2 may be converted from the normal mode NM to the pull-in mode PIM.

On the other hand, a bias voltage lower than the pull-in voltage Vpi may be applied to the first pixel P21 and the third pixel P23 of the second pixel row PR2. Accordingly, the operation mode of the ultrasonic generators superimposed on the first pixel P21 and the third pixel P23 of the second pixel row PR2 may be remained in the normal mode NM.

Here, if the scan voltage Vscan, the mode voltage Vmode and the setting voltage Vs satisfy condition (5), the operation mode of the ultrasonic generator corresponding to the pull-in pixel may be maintained in the pull-in mode while the pull-in coding operation for the pertinent coding row is processed. A pull-in pixel may be a pixel coded with a pull-in mode by the pull-in coding operation. In FIG. 9C, the second pixel P22 and the fourth pixel P24 of the second pixel row PR2 may each be a pull-in pixel.

$$Vpo < Vmode < Vpi \tag{5}$$

Accordingly, while the pull-in coding operation is performed for the second pixel row PR2, the operation mode of the ultrasonic generators superimposed on the pull-in pixels P22, P24 already coded with the pull-in mode may be maintained in the pull-in mode PIM.

Figure 9D:
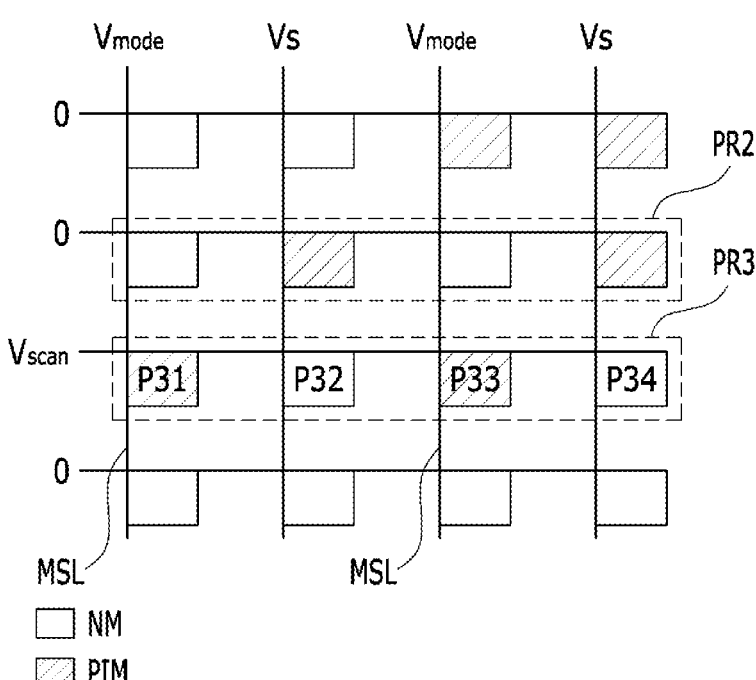

Referring to FIG. 9D, the second pixel row PR2 may be grounded. Then, the scan voltage Vscan may be applied to the first conductive line 210 to select the third pixel row PR3 as the coding row. Then, in order to pull-in code the first pixel P31 and the third pixel P33 of the third pixel row PR3, the first line and the third line of the plurality of first conductive lines 210 may be selected as the mode changing lines MSL. Moreover, the mode voltage Vmode may be applied to the first line and the third line of the plurality of first conductive lines 210.

Here, if the scan voltage Vscan, the mode voltage Vmode and the setting voltage Vs satisfy conditions (2) and (3), a bias voltage greater than the pull-in voltage may be applied to the first pixel P31 and the third pixel P33 of the third pixel row PR3. Accordingly, the operation mode of the ultrasonic generators superimposed on the first pixel P31 and the third pixel P33 of the third pixel row PR3 may be changed from the normal mode NM to the pull-in mode PIM.

On the other hand, a bias voltage lower than the pull-in voltage Vpi may be applied to the second pixel P32 and the fourth pixel P34 of the third pixel row PR3. Accordingly, the operation mode of the ultrasonic generators superimposed on the second pixel P32 and the fourth pixel P34 of the third pixel row PR3 may be maintained in the normal mode NM.

As in the case of FIG. 9C, the scan voltage Vscan, the mode voltage Vmode and the setting voltage Vs may satisfy conditions (4) and (5). Moreover, a secondary bias voltage smaller than the pull-in voltage Vpi may be applied to the ultrasonic generators superimposed on the first pixel P31 and the third pixel P33 of the third pixel row PR3 that have already been coded in the pull-in mode while the pull-in coding operation is processed for the third pixel row PR3. Therefore, the operation mode of the ultrasonic generators superimposed on the first pixel P31 and the third pixel P33 of the third pixel row PR3 may be maintained in the pull-in mode PIM.

Figure 9E:
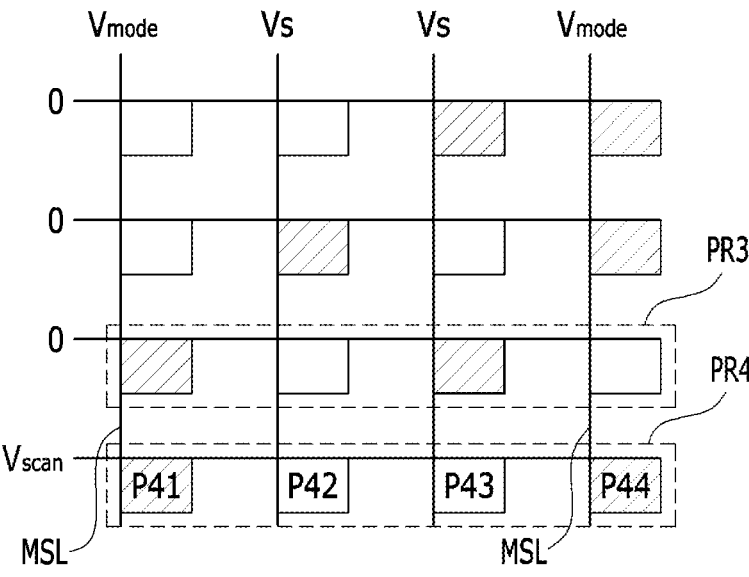

Referring to FIG. 9E, the third pixel row PR3 may be grounded. Then, the scan voltage Vscan may be applied to the fourth first conductive line of the plurality of first conductive lines 210 to select the fourth pixel row PR4 as the coding row. Then, in order to pull-in code the first pixel P41 and the fourth pixel P44 of the fourth pixel row PR4, the first conductive line and the fourth first conductive line of the plurality of first conductive lines 210 may be selected as the mode changing lines MSL. Moreover, the mode voltage Vmode may be applied to the first conductive line and the fourth first conductive line of the plurality of first conductive lines 210.

Here, if the scan voltage Vscan, the mode voltage Vmode and the setting voltage Vs satisfy conditions (2) and (3), a bias voltage greater than the pull-in voltage may be applied to the first pixel P41 and the fourth pixel P44 of the fourth pixel row PR4. Accordingly, the operation mode of the ultrasonic generators superimposed on the first pixel P41 and the fourth pixel P44 of the fourth pixel row PR4 may be changed from the normal mode NM to the pull-in mode PIM.

On the other hand, a bias voltage lower than the pull-in voltage Vpi may be applied to the second pixel P42 and the third pixel P43 of the fourth pixel row PR4. Accordingly, the operation mode of the ultrasonic generators superimposed on the second pixel P42 and the third pixel P43 of the fourth pixel row PR4 may be maintained in the normal mode NM.

As in the case of FIG. 9D, the scan voltage Vscan, the mode voltage Vmode and the setting voltage Vs may satisfy conditions (4) and (5). Accordingly, a secondary bias voltage smaller than the pull-in voltage Vpi may be applied to the ultrasonic generators superimposed on the first pixel P41 and the fourth pixel P44 of the fourth pixel row PR4 that have already been coded in the pull-in mode PIM while the pull-in coding operation is processed for the fourth pixel row PR4. Therefore, the operation mode of the ultrasonic generators superimposed on the first pixel P41 and the fourth pixel P44 of the fourth pixel row PR4 may be maintained in the pull-in mode PIM.

Figure 9F:
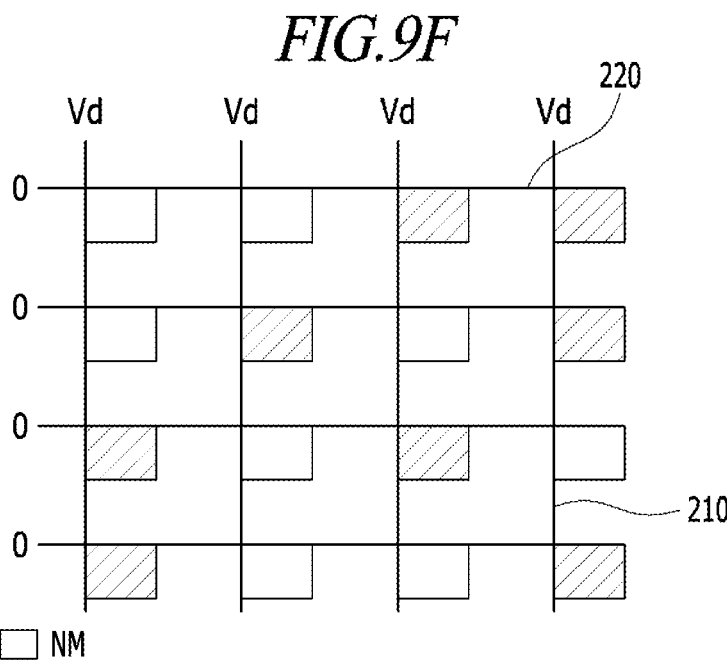

Referring to FIG. 9F, a drive-bias may be applied to the coding array 301, and the capacitances of the plurality of pixels may be identical to each other. Specifically, since the scan voltage Vscan and the mode voltage Vmode are simultaneously applied to the plurality of ultrasonic generators corresponding to a coding column CC, the bias voltages applied to the plurality of ultrasonic generators may be different from each other. In order to control the bias voltages applied to the plurality of ultrasonic generators to be identical to each other, a drive-bias satisfying condition (6) may be applied to the plurality of first conductive lines 210, and the second conductive lines 220 may be grounded.

$$Vpo < Vd < Vpi \qquad (6)$$

In condition (6), Vpo may be a pull-out voltage, and Vpi may be a pull-in voltage. Vd may be a drive-bias.

Specifically, if the drive-bias is smaller than the pull-in voltage and greater than the pull-out voltage, the operation mode of the ultrasonic generator corresponding to the pull-in pixel of the coding array 301 may be maintained in the pull-in mode PIM.

Then, when the drive signal, which is an AC signal, is applied to the coding array 301, to which the uniform drive-bias is applied, unit-ultrasonic waves may be generated at the active pixels AP. In the case where the frequency of the drive signal is the same as the first natural frequency, resonance may occur in the active pixels to generate ultrasonic waves having a great energy, and nearly no ultrasonic waves may be generated in the inactive pixels. The amplitude-modulated ultrasonic waves AMU may be generated by the synthesis of the plurality of ultrasonic waves generated in the plurality of active pixels AP of the coding array 301.

In the method of generating amplitude-modulated ultrasonic waves in accordance with an embodiment of the present disclosure, the plurality of ultrasonic generators may be coded with one of the normal mode and the pull-in mode to generate the coding array. Each of the plurality of ultrasonic generators may include at least one CMUT device. Each ultrasonic array may include a plurality of ultrasonic generators superimposed on one of the plurality of pixels. The coding array may include an active pixel and an inactive pixel.

When the drive signal having the same frequency as the natural frequency of the ultrasonic generator operating in the normal mode is applied to the coding array, unit-ultrasonic waves may be generated in the active pixels only, and no unit-ultrasonic waves may be generated in the inactive pixels. That is, a plurality of amplitude-modulated ultrasonic waves having different shapes of wavefront according to the pixel map may be generated.

The operation mode of the plurality of ultrasonic generators of the coding array may be changed according to the scan voltage, the mode voltage and the setting voltage. Therefore, with the present disclosure, the user may readily change the coding array 3001 by changing the scan voltage, the mode voltage and the setting voltage. Moreover, with the present disclosure, the user may change the shape of the wavefront of the amplitude-modulated ultrasonic waves AMU by changing the scan voltage, the mode voltage and the setting voltage.

Hitherto, certain preferred embodiments of the present disclosure have been described in detail, but anyone ordinarily skilled in the art to which the present disclosure pertains shall appreciate that there may be a variety of modifications and permutations of the present disclosure without departing from the technical ideas and scopes of the present disclosure that are defined in the appended claims.

What is claimed is:

1. A spatial ultrasound modulator, comprising:
   a signal line comprising a plurality of first conductive lines and a plurality of second conductive lines, the plurality of first conductive lines being arranged to be spaced apart from each other on a substrate, the plurality of second conductive lines being arranged to intersect the first conductive lines above the plurality of first conductive lines and to be spaced apart from each other;
   an ultrasonic array comprising a plurality of ultrasonic generators, each of the plurality of ultrasonic generators comprising at least one CMUT device and being superimposed on one of a plurality of pixels, which are intersection points of the plurality of first conductive lines and the plurality of second conductive lines, and generating unit-ultrasonic waves;
   a pixel coder configured to generate a coding array by determining an operation mode of each of the plurality of ultrasonic generators as one of a normal mode and a pull-in mode and comprising active pixels and inactive pixels; and
   an ultrasonic driver configured to drive the coding array to generate amplitude-modulated ultrasonic waves in which a wavefront may be transformed, the amplitude-modulated ultrasonic waves having a plurality of unit-ultrasonic waves synthesized therein.

2. The spatial ultrasound modulator of claim 1, wherein: the operation mode is one of a normal mode and a pull-in mode, when the operation mode is in the normal mode, the ultrasonic generator is configured to operate at a first natural frequency, and the pixel superimposed on the ultrasonic generator is configured to function as an active pixel, and when the operation mode is in the pull-in mode, the ultrasonic generator is configured to operate at a second natural frequency different from the first natural frequency, and the pixel superimposed on the ultrasonic generator is configured to function as an inactive pixel.

3. The spatial ultrasound modulator of claim 2, wherein the ultrasonic generator comprises a plurality of CMUT devices, the plurality of CMUT devices being configured to generate a plurality of fine ultrasonic waves, the unit-ultrasonic waves having the plurality of fine ultrasonic waves synthesized therein.

4. The spatial ultrasound modulator of claim 2, the pixel coder comprises:

an initialization driver configured to apply an initialization signal to the plurality of first conductive lines and the plurality of second conductive lines to initialize the operation mode of the plurality of ultrasonic generators to the normal mode;

a scanline setter configured to select one of the plurality of second conductive lines as a scan line and select a pixel row corresponding to the scan line as a coding row;

a mode line setter configured to select at least one of the plurality of first conductive lines as a mode changing line and select a pixel column of an ultrasonic array corresponding to the mode changing line as a coding column;

a pull-in coder configured to apply a scan signal to the scan line, apply a mode changing signal to the mode changing line, and perform a pull-in coding operation to code a coding target pixel in the pull-in mode using a potential difference between the scan signal and the mode changing signal, the coding target pixel being a pixel located at an intersection of the coding row and the coding column; and a timing controller configured to control operation timing of the scanline setter and the mode line setter to successively select one of the plurality of second conductive lines as a scan line and select a first conductive line of the plurality of first conductive lines corresponding to the coding target pixel as the mode changing line.

5. The spatial ultrasound modulator of claim 4, wherein the initialization signal comprises a first partial setting signal and a second partial setting signal, the first partial setting signal corresponding to a first partial setting voltage being applied to the plurality of first conductive lines, the second partial setting signal corresponding to a second partial setting voltage being applied to the plurality of second conductive lines, a setting voltage being a potential difference between the first partial setting voltage and the second partial setting voltage and satisfying condition (1) and being applied to the ultrasonic generator, $$Vpi < Vs = (Vs1 - Vs2) < Vpi \tag{1}$$

whereas Vpo is a pull-out voltage, and Vpi is a pull-in voltage, and Vs is a setting voltage, and Vs1 is a first partial setting voltage, and Vs2 is a second partial setting voltage.

6. The spatial ultrasound modulator of claim 5, wherein a scan voltage is a voltage of the scan signal, and a mode voltage is a voltage of the mode changing signal, and when the scan voltage and the mode voltage satisfy conditions (2) to (4), an operation mode of a ultrasonic generator superimposed on the coding target pixel among ultrasonic generators superimposed on the coding row is changed to a pull-in mode, and an operation mode of an ultrasonic generator not corresponding to the coding target pixel among ultrasonic generators superimposed on the coding row is kept in a normal mode, $$Vs - Vscan < Vpi \tag{2}$$

$$Vmode - Vscan > Vpi \tag{3}$$

$$Vmode < Vpi \tag{4}$$

whereas Vs is a setting voltage, and Vscan is a scan voltage, and Vmode is a mode voltage.

7. The spatial ultrasound modulator of claim 6, wherein, when the mode voltage satisfies condition (5), an operation mode of an ultrasonic generator superimposed on the pull-in pixel is maintained in the pull-in mode while a pull-in coding operation is performed in a coding row corresponding to a pull-in pixel, the pull-in pixel being a pixel that has been already coded in the pull-in mode through the pull-in coding operation, $$Vpi < Vmode < Vpi. \tag{5}$$

8. The spatial ultrasound modulator of claim 4, wherein the pixel coder further comprises a pixel reset unit configured to reset a coded pixel.

9. The spatial ultrasound modulator of claim 4, wherein the ultrasonic driver comprises a drive setting unit and a driving unit, wherein the drive setting unit is configured to control bias voltages applied to a plurality of ultrasonic generators of the coding array to be the same with each other by applying a drive-bias to the coding array, and wherein the driving unit is configured to control an ultrasonic generator corresponding to the active pixel to generate the unit ultrasonic waves by applying a drive signal to the coding array.

10. The spatial ultrasound modulator of claim 9, wherein the drive setting unit is configured to apply a drive-bias satisfying condition (6) to the plurality of first conductive lines and control the plurality of second conductive lines to be grounded, $$Vpo < Vd < Vpi \tag{6}$$

whereas Vpo is a pull-out voltage, and Vpi is a pull-in voltage, and Vd is a drive-bias.

11. The spatial ultrasound modulator of claim 10, wherein a frequency of the drive signal is the same as a natural frequency of an ultrasonic generator of which the operation mode is the normal mode.

12. The spatial ultrasound modulator of claim 1, further comprising a waveform controller, wherein the waveform controller is configured to control the pixel coder to change the coding array according to wavefront information and control the ultrasonic driver to generate the amplitude-modulated ultrasonic waves according to the changed coding array to deform the wavefront of the amplitude-modulated ultrasonic waves in real time.

13. An ultrasonic apparatus, comprising:

a wavefront information setter configured to set wavefront information corresponding to incident waves, the incident waves being spatially modulated ultrasonic waves incident on a target object;

a spatial ultrasound modulator comprising a pixel coder and an ultrasonic driver, the pixel coder being configured to code an ultrasonic array based on the wavefront information to generate a coding array, the coding array comprising an active pixel and an inactive pixel, the ultrasonic array comprising a plurality of ultrasonic generators, each of the plurality of ultrasonic generators comprising at least one capacitive micromachined ultrasonic transducer (CMUT) device and being superimposed on one of a plurality of pixels, the ultrasonic driver being configured to drive the coding array to generate amplitude-modulated ultrasonic waves having a wavefront corresponding to the wavefront information; and a response detection unit configured to detect a response of the target object to the incident waves.

14. The ultrasonic apparatus of claim 13, wherein the spatial ultrasound modulator further comprises a signal line comprising a plurality of first conductive lines and a plurality of second conductive lines, and wherein the plurality of first conductive lines are arranged to be spaced apart from each other on a substrate, and the plurality of second conductive lines are arranged to intersect the plurality of first conductive lines above the plurality of first conductive lines and to be spaced apart from each other, and a bias voltage applied to the ultrasonic generator is a potential difference between one of the plurality of first conductive lines and one of the plurality of second conductive lines.

15. The ultrasonic apparatus of claim 14, wherein the pixel coder comprises:

an initialization driver configured to apply an initialization signal to the plurality of first conductive lines and the plurality of second conductive lines to initialize an operation mode of each of the plurality of ultrasonic generators to a normal mode;

a scanline setter configured to select one of the plurality of second conductive lines as a scan line for transmitting a scan signal and select a pixel row, which is an ultrasonic generators among the plurality of ultrasonic generators corresponding to the scan line, as a coding row;

a mode line setter configured to select at least one of the plurality of first conductive lines as a mode changing line for transmitting a mode changing signal, the mode changing signal being for changing an operation mode of the ultrasonic generator to one of the normal mode and the pull-in mode, the mode line setter configured to select a pixel column, which is ultrasonic generators among the plurality of ultrasonic generators corresponding to the mode changing line, as a coding column;

a pull-in coder configured to apply a scan signal to the scan line, apply a mode changing signal to the mode changing line, and perform a pull-in coding operation, which is configured to code a coding target pixel in the pull-in mode using a potential difference between the scan signal and the mode changing signal, the coding target pixel being a pixel located at an intersection of the coding row and the coding column; and a timing controller configured to control the scanline setter to successively select each of the plurality of second conductive lines as the scan line, control the mode line setter to select a first conductive line of the plurality of the first conductive lines corresponding to a coding target pixel as the mode changing line, and control the pull-in coder to perform a pull-in coding operation.

16. The ultrasonic apparatus of claim 15, wherein the initialization signal comprises a first partial setting signal and a second partial setting signal, the first partial setting signal corresponding to a first partial setting voltage being simultaneously applied to the plurality of first conductive lines, the second partial setting signal corresponding to a second partial setting voltage being simultaneously applied to the plurality of second conductive lines, a setting voltage being a potential difference between the first partial setting voltage and the second partial setting voltage and satisfying condition (1) and being applied to the ultrasonic generator, $$Vpi < Vs = (Vs1 - Vs2) < Vpi \tag{1}$$

whereas Vpo is a pull-out voltage, and Vpi is a pull-in voltage, and Vs is a setting voltage, and Vs1 is a first partial setting voltage, and Vs2 is a second partial setting voltage, wherein a scan voltage is a voltage of the scan signal, and a mode voltage is a voltage of the mode changing signal, and when the scan voltage and the mode voltage satisfy conditions (2) to (4), a bias voltage greater than the pull-in voltage is applied to an ultrasonic generator corresponding to the coding target pixel to have an operation mode of the ultrasonic generator changed to a pull-in mode and have an operation mode of an ultrasonic generator not corresponding to the coding target pixel maintained in the normal mode, $$Vs - Vscan < Vpi \tag{2}$$

$$Vmode - Vscan > Vpi \tag{3}$$

$$Vmode < Vpi \tag{4}$$

whereas Vs is a setting voltage, and Vscan is a scan voltage, and Vmode is a mode voltage, and wherein, when the mode voltage satisfies condition (5), an operation mode of an ultrasonic generator superimposed on a pull-in pixel is maintained in the pull-in mode while a pull-in coding operation is performed in a coding row corresponding to the pull-in pixel, the pull-in pixel being a pixel that has been already coded in the pull-in mode through the pull-in coding operation, $$Vpo < Vmode < Vpi. \qquad (5)$$

17. The ultrasonic apparatus of claim 16, wherein the ultrasonic driver comprises a drive setting unit and a driving unit, wherein the drive setting unit is configured to apply a drive-bias satisfying condition (6) to the plurality of first conductive lines and control the plurality of second conductive lines to be grounded, $$Vpo < Vd < Vpi \qquad (6)$$

whereas Vd is a drive-bias, and wherein the driving unit is configured to control an ultrasonic generator corresponding to the active pixel to generate ultrasonic waves by applying a drive signal to the coding array.

18. The ultrasonic apparatus of claim 17, wherein the drive signal comprises an AC signal, and a frequency of the AC signal is the same as a natural frequency of an ultrasonic generator of which the operation mode is the normal mode.

19. A method of generating amplitude-modulated ultrasonic waves, the method comprising:

step 1, in which an ultrasonic array comprises a plurality of pixel rows and a plurality of pixel columns, each the pixel rows and the pixel columns comprises a plurality of ultrasonic generators, each of the plurality of ultrasonic generators is superimposed on one of a plurality of pixels, and an ultrasonic array is initialized by a setting voltage such that the plurality of ultrasonic generators operate in a normal mode;

step 2, in which the plurality of pixel rows are successively selected, one by one, as a coding row, and at least one pixel column of the plurality of pixel columns that corresponds to a coding target pixel is selected as a coding column;

step 3, in which a coding array comprises active pixels and inactive pixels, and when the operation mode is in the normal mode, an ultrasonic generator operates at a first natural frequency, and a pixel superimposed on the ultrasonic generator functions as an active pixel, and when the operation mode is a pull-in mode, an ultrasonic generator operates at a second natural frequency different from the first natural frequency, and a pixel superimposed on the ultrasonic generator functions as an inactive pixel, and whenever a coding row is selected, a scan voltage and a mode voltage are applied to the coding row and the coding column, respectively, and an operation mode of an ultrasonic generator superimposed on the coding target pixel is changed to the pull-in mode and the coding array is generated; and step 4, in which the coding array generates amplitude-modulated ultrasonic waves in which a wavefront may be modified, and the amplitude-modulated ultrasonic waves are a synthesized plurality of unit-ultrasonic waves, each of which is generated by an ultrasonic generator superimposed on the active pixel.

20. The method of claim 19, wherein, in the step 1, the plurality of pixel rows are grounded, and the setting voltage satisfying condition (1) is applied to the plurality of pixel columns, $$Vpo < Vs = (Vs1 - Vs2) < Vpi \qquad (1)$$

whereas Vpo is a pull-out voltage, Vpi is a pull-in voltage, and Vs is a setting voltage.

21. The method of claim 20, wherein, in the step 3, when the setting voltage, the scan voltage and the mode voltage satisfy conditions (2) to (4), an operation mode of an ultrasonic generator of a plurality of ultrasonic generators superimposed on the coding row that is not superimposed on the coding target pixel is maintained in the normal mode, $$Vs - Vscan < Vpi \qquad (2)$$
$$Vmode - Vscan > Vpi \qquad (3)$$
$$Vmode < Vpi \qquad (4)$$

whereas, in conditions (2) and (4), Vscan is a scan voltage, and Vmode is a mode voltage.

22. The method of claim 21, wherein, when the mode voltage satisfies condition (5), an operation mode of an ultrasonic generator superimposed on a pull-in pixel is maintained in the pull-in mode while a pull-in coding operation is performed for a coding row corresponding to the coding target pixel, and the pull-in pixel is a pixel that has been already coded in the pull-in mode through the pull-in coding operation, $$Vpo < Vmode < Vpi. \qquad (5)$$

23. The method of claim 19, further comprising step 3-1, in which the coding row is grounded, and a drive-bias satisfying condition (6) is applied to the coding column such that an operation mode of an ultrasonic generator superimposed on a pull-in pixel is maintained in a pull-in mode, wherein the step 3-1 is performed after the step 3 and before the step 4, and wherein the pull-in pixel is a pixel that has been already coded in the pull-in mode through a pull-in coding operation, $$Vpo < Vd < Vpi \qquad (6)$$

whereas Vd is a drive-bias.

24. The method of claim 19, wherein, in the step 4, a drive signal is applied to the coding array, and the drive signal is an AC signal having a same frequency as the first natural frequency.

* * * * *